(12) United States Patent
Piryatinsky et al.

(10) Patent No.: US 8,580,819 B2
(45) Date of Patent: Nov. 12, 2013

(54) DEUTERATED N-ETHYL-N-PHENYL-1,2-DIHYDRO-4-HYDROXY-5-CHLORO-1-METHYL-2-OXOQUINOLINE-3-CARBOXAMIDE, SALTS AND USES THEREOF

(75) Inventors: Victor Piryatinsky, Netanya (IL); Avital Laxer, Tel-Aviv (IL)

(73) Assignee: Teva Pharmaceutical Industries Ltd., Petach-Tikva (IL)

(*) Notice: Subject to any disclaimer, the term of this patent is extended or adjusted under 35 U.S.C. 154(b) by 2 days.

(21) Appl. No.: 13/178,842

(22) Filed: Jul. 8, 2011

(65) Prior Publication Data
US 2012/0010238 A1    Jan. 12, 2012

Related U.S. Application Data

(60) Provisional application No. 61/399,297, filed on Jul. 9, 2010.

(51) Int. Cl.
*A61K 31/04* (2006.01)
*C07D 215/38* (2006.01)

(52) U.S. Cl.
USPC .......................................... 514/312; 546/155

(58) Field of Classification Search
USPC .......................................... 514/312; 546/155
See application file for complete search history.

(56) References Cited

U.S. PATENT DOCUMENTS

| | | | |
|---|---|---|---|
| 4,547,511 A | 10/1985 | Eriksoo et al. | |
| 6,077,851 A * | 6/2000 | Bjork et al. | 514/312 |
| 6,121,287 A | 9/2000 | Bjork et al. | |
| 6,133,285 A | 10/2000 | Bjork et al. | |
| 6,593,343 B2 | 7/2003 | Bjork et al. | |
| 6,605,616 B1 | 8/2003 | Bjork et al. | |
| 6,875,869 B2 | 4/2005 | Jansson | |
| 7,514,068 B2 | 4/2009 | Tung et al. | |
| 7,528,131 B2 | 5/2009 | Persichetti et al. | |
| 7,560,557 B2 | 7/2009 | Jansson | |
| 7,589,208 B2 | 9/2009 | Jansson et al. | |
| 7,884,208 B2 | 2/2011 | Frenkel et al. | |
| 7,989,473 B2 | 8/2011 | Patashnik et al. | |
| 8,178,127 B2 | 5/2012 | Safadi et al. | |
| 8,252,933 B2 | 8/2012 | Gant et al. | |
| 2002/0173520 A1 | 11/2002 | Bjork et al. | |
| 2005/0192315 A1 | 9/2005 | Jansson et al. | |
| 2005/0215586 A1 | 9/2005 | Jansson et al. | |
| 2009/0232889 A1 | 9/2009 | Jansson et al. | |
| 2010/0055072 A1* | 3/2010 | Gant et al. | 424/85.6 |
| 2010/0322900 A1 | 12/2010 | Tarcic et al. | |
| 2011/0027219 A1 | 2/2011 | Tarcic et al. | |
| 2011/0034508 A1 | 2/2011 | Hayardeny et al. | |
| 2011/0112141 A1 | 5/2011 | Frenkel et al. | |
| 2011/0118308 A1 | 5/2011 | Frenkel et al. | |
| 2011/0217295 A1 | 9/2011 | Haviv et al. | |
| 2011/0218179 A1 | 9/2011 | Haviv et al. | |
| 2011/0218203 A1 | 9/2011 | Kaye et al. | |
| 2012/0010239 A1 | 1/2012 | Fristedt | |
| 2012/0142730 A1 | 6/2012 | Tarcic et al. | |
| 2012/0225124 A1 | 9/2012 | Safadi et al. | |

FOREIGN PATENT DOCUMENTS

| | | |
|---|---|---|
| EP | 1073639 | 2/2001 |
| EP | 1095021 | 5/2001 |
| EP | 1097139 | 5/2001 |
| EP | 1511732 | 3/2005 |
| EP | 1720531 | 11/2006 |
| WO | WO 99/55678 | 11/1999 |
| WO | WO 00/03991 | 1/2000 |
| WO | WO 00/03992 | 1/2000 |
| WO | WO 00/74654 | 12/2000 |
| WO | WO 03/106424 | 12/2003 |
| WO | WO 2005/074899 | 8/2005 |

OTHER PUBLICATIONS

Kushner, Canadian J Physiology and Pharm, Feb. 1999, vol. 77(2), pp. 79-88.*
PCT International Search Report issued Dec. 9, 2011 in connection with PCT International Application No. PCT/US11/43383, filed Jul. 8, 2011.
Written Opinion of the International Searching Authority issued Nov. 29, 2011 in connection with PCT International Application No. PCT/US11/43383, filed Jul. 8, 2011.
PCT International Search Report issued Nov. 21, 2011 in connection with PCT International Application No. PCT/US11/43391, filed Jul. 8, 2011.
Written Opinion of the International Searching Authority issued Nov. 29, 2011 in connection with PCT International Application No. PCT/US11/43391, filed Jul. 8, 2011.
PCT International Preliminary Report on Patentability issued Mar. 8, 2011 in connection with PCT International Application No. PCT/US2009/055692, filed Sep. 2, 2009.
PCT International Search Report issued Apr. 21, 2010 in connection with PCT International Application No. PCT/US2009/055692, filed Sep. 2, 2009.
Written Opinion of the International Searching Authority issued Apr. 21, 2010 in connection with PCT International Application No. PCT/US2009/055692.
European Search Report completed Aug. 10, 2011 in connection with European Patent No. EP 09812145.
Notice of Allowance issued by the U.S. Patent and Trademark Office on Apr. 27, 2012 in connection with U.S. Appl. No. 12/552,663.
Office Action issued by the U.S. Patent and Trademark Office on Jan. 12, 2012 in connection with U.S. Appl. No. 12/552,663.
Amendment filed with the U.S. Patent and Trademark Office on Apr. 12, 2012 in connection with U.S. Appl. No. 12/552,663.

(Continued)

Primary Examiner — D M Seaman
(74) Attorney, Agent, or Firm — John P. White; Gary J. Gershik; Cooper & Dunham LLP

(57) ABSTRACT

The subject invention provides deuterated N-ethyl-N-phenyl-1,2-dihydro-4-hydroxy-5-chloro-1-methyl-2-oxoquinoline-3-carboxamide, its salts and uses.

29 Claims, 3 Drawing Sheets

(56) References Cited

OTHER PUBLICATIONS

Jönsson S. et al. "Synthesis and Biological Evaluation of New 1,2-Dihydro-4-hydroxy-2-oxo-3-quinolinecarboxamides for Treatment . . . " J. of Medicial Chemistry, vol. 47, 2075-2088, 2004.
Wennerbert et al. (2007) "Development of a Practical and Reliable Synthesis of Laquinimod", Organic Process Research & Development 11:674-680.
Tuvesson et al. (2005) "Cytochrome P450 3A4 is the Major Enzyme Responsible for the Metabolism of Laquinimod . . . " Drug Metabolism and Disposition 33(6):866-872.
International Preliminary Report on Patentability issued on Jan. 15, 2013 in connection with PCT International Application No. PCT/US2011/043383, filed on Jul. 8, 2011.

* cited by examiner

DEUTERATED N-ETHYL-N-PHENYL-1,2-DIHYDRO-4-HYDROXY-5-CHLORO-1-METHYL-2-OXOQUINOLINE-3-CARBOXAMIDE, SALTS AND USES THEREOF

This application claims benefit of U.S. Provisional Application No. 61/399,297, filed Jul. 9, 2010, the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2-dihydro-4-hydroxy-5-chloro-1-methyl-2-oxoquinoline-3-carboxamide, and its Chemical Registry number is 248281-84-7. The processes of synthesis of laquinimod and the preparation of its sodium salt are disclosed in U.S. Pat. No. 6,077,851. An additional process of synthesis of laquinimod is disclosed in U.S. Pat. No. 6,875,869.

Pharmaceutical compositions comprising laquinimod sodium are disclosed in PCT International Application Publication No. WO 2005/074899.

Laquinimod sodium is a novel synthetic compound with high oral bioavailability, which has been suggested as an oral formulation for the treatment of Multiple Sclerosis (MS). (Polman, C. et al., (2005) "Treatment with laquinimod reduces development of active MRI lesions in relapsing MS", Neurology. 64:987-991; Sandberg-Wollheim M, et al. (2005) "48-week open safety study with high-dose oral laquinimod in patients", *Mult Scler.* 11:S154) Studies have also shown that laquinimod can reduce development of active MRI lesions in relapsing MS. (Polman, C. et al., (2005) "Treatment with laquinimod reduces development of active MRI lesions in relapsing MS", Neurology. 64:987-991).

PCT International Application Publication No. WO 2010/028015 proposes deuterium-enriched variants of laquinimod. However, WO 2010/028015 cautions that, "[m]etabolic switching can lead to different proportions of known metabolites as well as altogether new metabolites" and such "new metabolic profile may impart more or less toxicity" which "are not predictable a priori for any drug class". Thus, WO 2010/028015 does not provide at least the dosage for administration of the deuterium-enriched variants of laquinimod, and does not disclose the metabolic profile.

SUMMARY OF THE INVENTION

The subject invention provides a method of treating a human subject afflicted with an autoimmune disease comprising administering to the human subject 0.2 mg-2.0 mg per day of a deuterium-enriched compound having the structure:

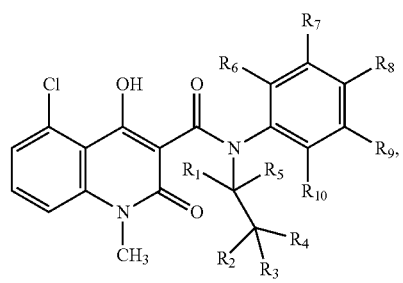

wherein each of R1-R10 is independently H or D, and at least one of R1-R10 is D, or a pharmaceutically acceptable salt thereof, effective to treat the subject.

The subject invention also provides a method of inducing reduced formation of optionally deuterated 5-chloro-4-hydroxy-1-methyl-2-oxo-N-phenyl-1,2-dihydroquinoline-3-carboxamide in a human subject comprising administering to the human subject a therapeutically effective amount of a deuterium-enriched compound having the structure:

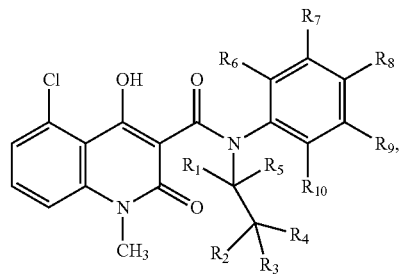

wherein each of R1-R10 is independently H or D, and at least one of R1-R10 is D, or a pharmaceutically acceptable salt thereof,
wherein the reduced formation is relative to formation of 5-chloro-4-hydroxy-1-methyl-2-oxo-N-phenyl-1,2-dihydroquinoline-3-carboxamide upon administration of an equivalent molar amount of non-deuterium-enriched laquinimod.

The subject invention further provides a mixture of at least two deuterium-enriched compounds, each compound having the structure:

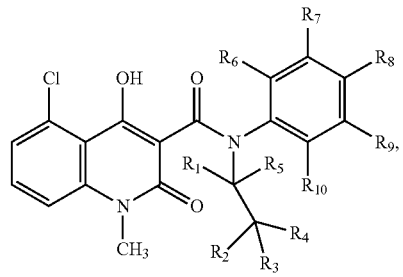

wherein each of R1-R10 is independently H or D, and each of the at least two deuterium-enriched compounds contains D at a different R1-R10,
or pharmaceutically acceptable salts thereof.

The subject invention yet further provides a pharmaceutical composition comprising the mixture described herein, or a pharmaceutically acceptable salt thereof, and a pharmaceutically acceptable carrier.

The subject invention yet further provides a pharmaceutical composition comprising a mixture of:
a) deuterium-enriched laquinimod or a pharmaceutically acceptable salt thereof;
b) at least one pharmaceutically acceptable carrier; and
c) a compound having the structure:

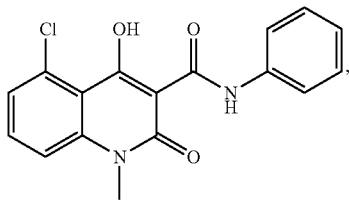 [SMILES: Cn1c(=O)c(C(=O)Nc2ccccc2)c(O)c2c(Cl)cccc21]

present in an amount which is less than 0.1% based on the combined weight of the compound and deuterium-enriched laquinimod.

The subject invention yet further provides a process for preparing the pharmaceutical composition described herein, the process comprises:
a) obtaining a batch of deuterium-enriched laquinimod or a pharmaceutically acceptable salt thereof;
b) determining by apparatus the total amount of optionally deuterated 5-chloro-4-hydroxy-1-methyl-2-oxo-N-phenyl-1,2-dihydroquinoline-3-carboxamide present in the batch of deuterium-enriched laquinimod or a pharmaceutically acceptable salt thereof; and
c) preparing the pharmaceutical composition using the batch only if the batch is determined to have less than 0.1% by weight of optionally deuterated 5-chloro-4-hydroxy-1-methyl-2-oxo-N-phenyl-1,2-dihydroquinoline-3-carboxamide.

The subject invention yet further provides a process for producing a validated batch of the pharmaceutical composition described herein for distribution, the process comprises:
a) obtaining a batch of the pharmaceutical composition;
b) determining by apparatus the total amount of optionally deuterated 5-chloro-4-hydroxy-1-methyl-2-oxo-N-phenyl-1,2-dihydroquinoline-3-carboxamide in a sample of the batch; and
c) validating the batch for distribution only if the sample of the batch is determined to contain less than 0.1% by weight of optionally deuterated 5-chloro-4-hydroxy-1-methyl-2-oxo-N-phenyl-1,2-dihydroquinoline-3-carboxamide relative to the combined weight of laquinimod and 5-chloro-4-hydroxy-1-methyl-2-oxo-N-phenyl-1,2-dihydroquinoline-3-carboxamide.

The subject invention yet further provides a deuterium-enriched compound having the structure:

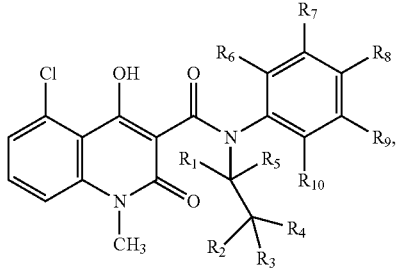

wherein each of R1-R10 is independently H or D, and at least one of R1-R10 is D, or a pharmaceutically acceptable salt thereof,
for use in an amount of 0.2 mg-2 mg per day in treating an autoimmune disease in a human subject.

DETAILED DESCRIPTION OF THE INVENTION

Figure 1:
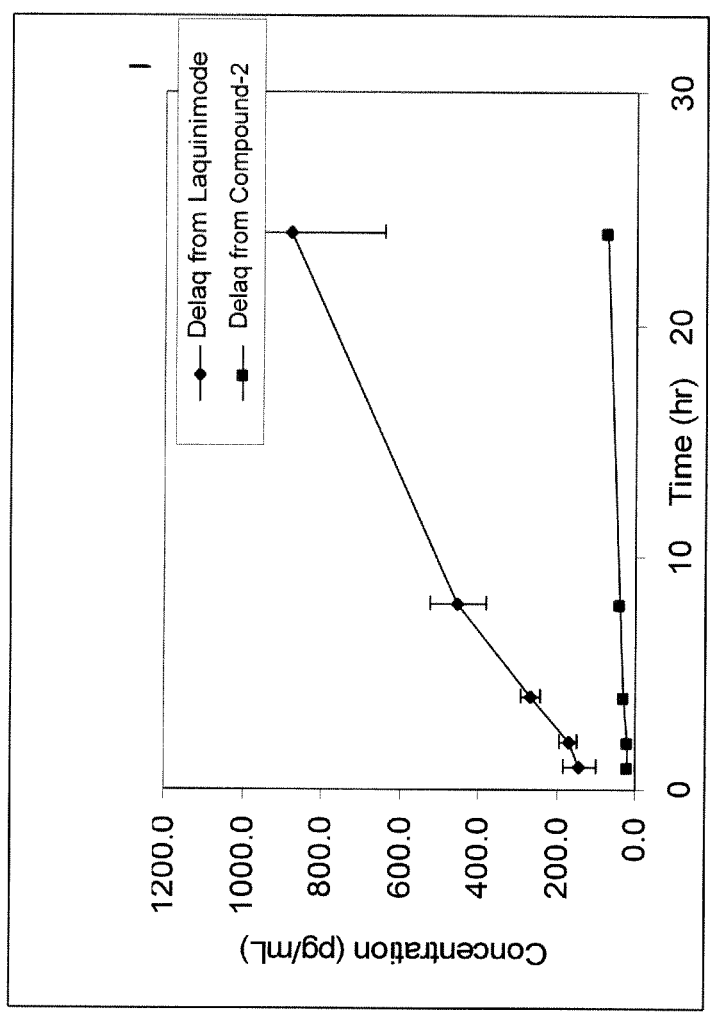
FIG. 1 shows the average plasma concentration-time profile for DELAQ formed from laquinimod vs. Compound 2 following oral administration to rats at 0.2 mg/kg.

The subject invention provides a method of treating a human subject afflicted with an autoimmune disease comprising administering to the human subject 0.2 mg-2.0 mg per day of a deuterium-enriched compound having the structure:

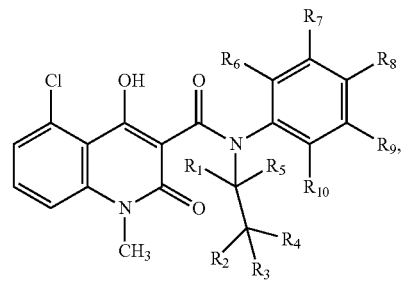

wherein each of R1-R10 is independently H or D, and at least one of R1-R10 is D, or a pharmaceutically acceptable salt thereof, effective to treat the subject.

In an embodiment of the method, the deuterium-enriched compound is

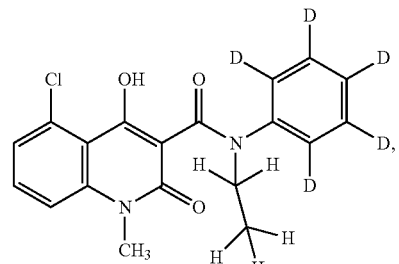

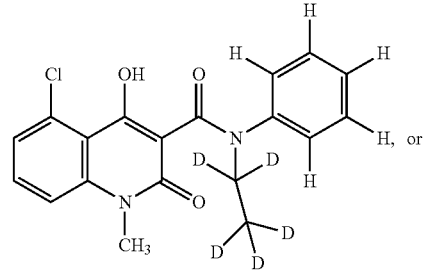

-continued

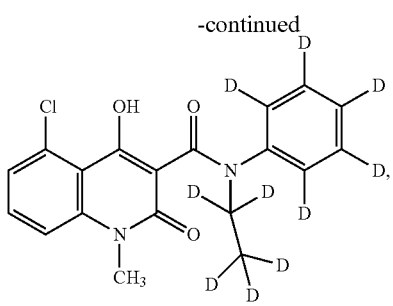

or a pharmaceutically acceptable salt thereof.

In another embodiment of the method, the deuterium-enriched compound is

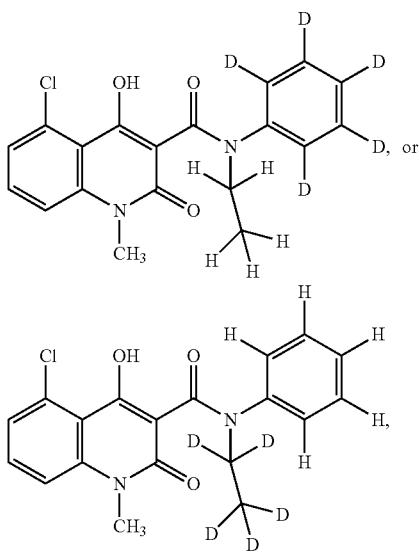

or a pharmaceutically acceptable salt thereof.

In yet another embodiment of the method, the deuterium-enriched compound is

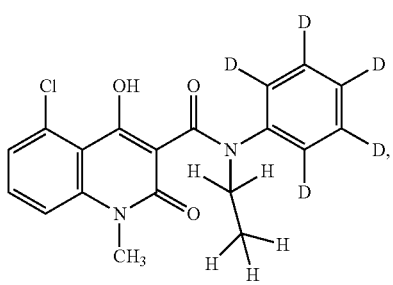

or a pharmaceutically acceptable salt thereof.

In yet another embodiment of the method, the autoimmune disease is Multiple Sclerosis, Systemic Lupus Erythematosus, lupus nephritis, lupus arthritis, Crohn's Disease or Rheumatoid arthritis.

In yet another embodiment of the method, the autoimmune disease is Multiple Sclerosis.

In yet another embodiment of the method, administration of the deuterium-enriched compound is more effective in treating the autoimmune disease than administration of an equivalent molar amount of non-deuterium-enriched laquinimod.

In yet another embodiment of the method, the level of optionally deuterated 5-chloro-4-hydroxy-1-methyl-2-oxo-N-phenyl-1,2-dihydroquinoline-3-carboxamide formed in the human subject upon administration of the deuterium-enriched compound is reduced, compared to the level of 5-chloro-4-hydroxy-1-methyl-2-oxo-N-phenyl-1,2-dihydroquinoline-3-carboxamide formed when an equivalent molar amount of non-deuterium-enriched laquinimod is administered to the human subject.

In yet another embodiment of the method, the level of optionally deuterated 5-chloro-4-hydroxy-1-methyl-2-oxo-N-phenyl-1,2-dihydroquinoline-3-carboxamide is reduced by at least 50%.

In yet another embodiment of the method, the level of optionally deuterated 5-chloro-4-hydroxy-1-methyl-2-oxo-N-phenyl-1,2-dihydroquinoline-3-carboxamide is reduced by at least 90%.

The subject invention also provides a method of inducing reduced formation of optionally deuterated 5-chloro-4-hydroxy-1-methyl-2-oxo-N-phenyl-1,2-dihydroquinoline-3-carboxamide in a human subject comprising administering to the human subject a therapeutically effective amount of a deuterium-enriched compound having the structure:

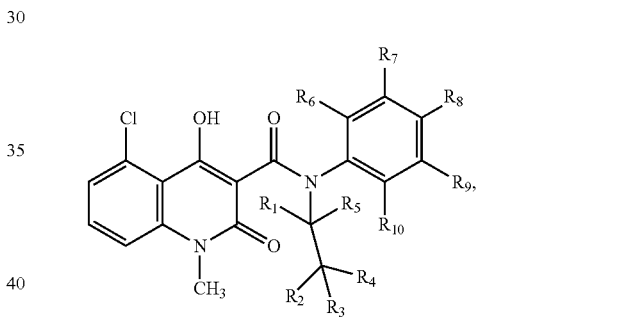

wherein each of $R_1$-$R_{10}$ is independently H or D, and at least one of $R_1$-$R_{10}$ is D, or a pharmaceutically acceptable salt thereof, wherein the reduced formation is relative to formation of 5-chloro-4-hydroxy-1-methyl-2-oxo-N-phenyl-1,2-dihydroquinoline-3-carboxamide upon administration of an equivalent molar amount of non-deuterium-enriched laquinimod.

In an embodiment of the method, the level of optionally deuterated 5-chloro-4-hydroxy-1-methyl-2-oxo-N-phenyl-1,2-dihydroquinoline-3-carboxamide is reduced by at least 50%, compared to the level of 5-chloro-4-hydroxy-1-methyl-2-oxo-N-phenyl-1,2-dihydroquinoline-3-carboxamide formed when an equivalent molar amount of non-deuterium-enriched laquinimod is administered to the human subject.

In another embodiment of the method, the level of optionally deuterated 5-chloro-4-hydroxy-1-methyl-2-oxo-N-phenyl-1,2-dihydroquinoline-3-carboxamide is reduced by at least 90%.

The subject invention further provides a mixture of at least two deuterium-enriched compounds, each compound having the structure:

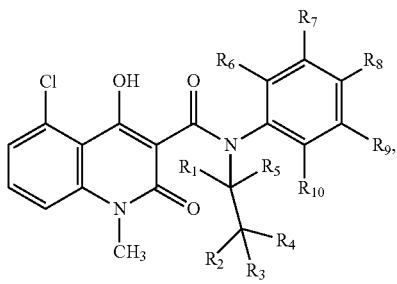

wherein each of R1-R10 is independently H or D, and each of the at least two deuterium-enriched compounds contains D at a different R1-R10,
or pharmaceutically acceptable salts thereof.

In an embodiment of the mixture, one of the at least two deuterium-enriched compounds has the structure:

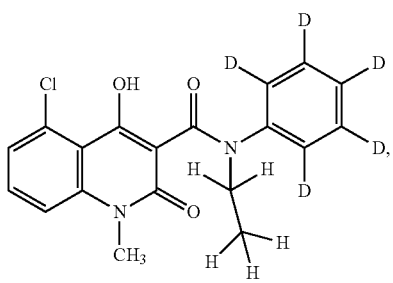

or pharmaceutically acceptable salts thereof.

In another embodiment of the mixture, one of the at least two deuterium-enriched compounds has the structure:

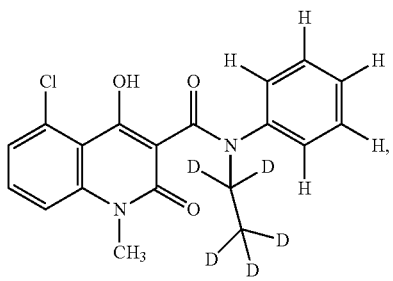

or pharmaceutically acceptable salts thereof.

In yet another embodiment of the mixture, one of the at least two deuterium-enriched compounds has the structure:

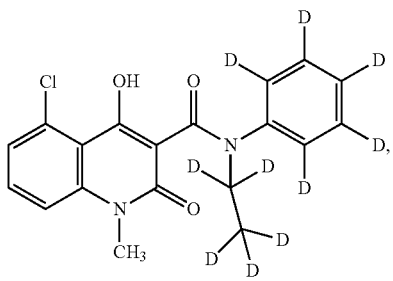

or pharmaceutically acceptable salts thereof.

The subject invention yet further provides a pharmaceutical composition comprising the mixture described herein, or a pharmaceutically acceptable salt thereof, and a pharmaceutically acceptable carrier.

The subject invention yet further provides a pharmaceutical composition comprising a mixture of:
a) deuterium-enriched laquinimod or a pharmaceutically acceptable salt thereof;
b) at least one pharmaceutically acceptable carrier; and
c) a compound having the structure:

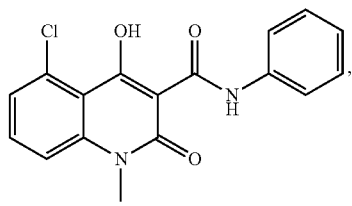 [SMILES: Cn1c(=O)c(C(=O)Nc2ccccc2)c(O)c2c(Cl)cccc21]

present in an amount which is less than 0.1% based on the combined weight of the compound and deuterium-enriched laquinimod.

In an embodiment of the pharmaceutical composition, the compound is present in an amount less than 3 ppm or less than 2 ppm based on the combined weight of the compound and deuterium-enriched laquinimod.

In another embodiment of the pharmaceutical composition, the deuterium-enriched laquinimod has the structure:

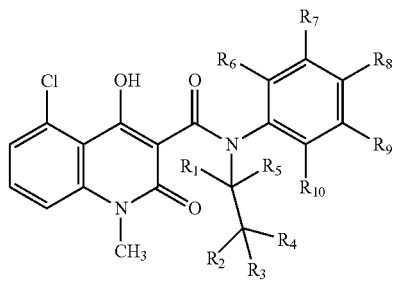

wherein each of R1-R10 is independently H or D, and at least one of R1-R10 is D,
or a pharmaceutically acceptable salt thereof.

In yet another embodiment of the pharmaceutical composition, in the deuterium-enriched laquinimod, each of R1-R5 is D and each of R6-R10 is H, or a pharmaceutically acceptable salt thereof.

In yet another embodiment of the pharmaceutical composition, in the deuterium-enriched laquinimod, each of R1-R5 is H and each of R6-R10 is D, or a pharmaceutically acceptable salt thereof.

In yet another embodiment of the pharmaceutical composition, in the deuterium-enriched laquinimod, each of R1-R10 is D, or a pharmaceutically acceptable salt thereof.

In yet another embodiment of the pharmaceutical composition, the pharmaceutical composition is in the form of a tablet.

In yet another embodiment of the pharmaceutical composition, when ingested by a human subject, the pharmaceutical composition provides a reduced level of optionally deuterated 5-chloro-4-hydroxy-1-methyl-2-oxo-N-phenyl-1,2-dihydroquinoline-3-carboxamide formed in the human subject, relative to the level of 5-chloro-4-hydroxy-1-methyl-2-oxo-N- phenyl-1,2-dihydroquinoline-3-carboxamide formed when an equivalent molar amount of non-deuterium-enriched laquinimod is ingested by the human subject.

The subject invention yet further provides a process for preparing the pharmaceutical composition described herein, the process comprises:
a) obtaining a batch of deuterium-enriched laquinimod or a pharmaceutically acceptable salt thereof;
b) determining by apparatus the total amount of optionally deuterated 5-chloro-4-hydroxy-1-methyl-2-oxo-N-phenyl-1,2-dihydroquinoline-3-carboxamide present in the batch of deuterium-enriched laquinimod or a pharmaceutically acceptable salt thereof; and
c) preparing the pharmaceutical composition using the batch only if the batch is determined to have less than 0.1% by weight of optionally deuterated 5-chloro-4-hydroxy-1-methyl-2-oxo-N-phenyl-1,2-dihydroquinoline-3-carboxamide.

The subject invention yet further provides a process for producing a validated batch of the pharmaceutical composition described herein for distribution, the process comprises:
a) obtaining a batch of the pharmaceutical composition;
b) determining by apparatus the total amount of optionally deuterated 5-chloro-4-hydroxy-1-methyl-2-oxo-N-phenyl-1,2-dihydroquinoline-3-carboxamide in a sample of the batch; and
c) validating the batch for distribution only if the sample of the batch is determined to contain less than 0.1% by weight of optionally deuterated 5-chloro-4-hydroxy-1-methyl-2-oxo-N-phenyl-1,2-dihydroquinoline-3-carboxamide relative to the combined weight of laquinimod and optionally deuterated 5-chloro-4-hydroxy-1-methyl-2-oxo-N-phenyl-1,2-dihydroquinoline-3-carboxamide.

The subject invention yet further provides a deuterium-enriched compound having the structure:

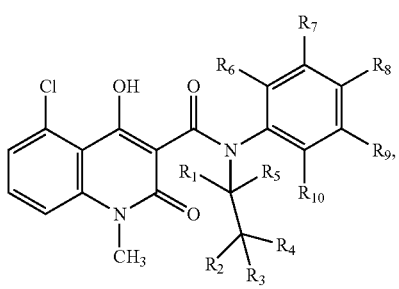

wherein each of $R_1$-$R_{10}$ is independently H or D, and at least one of $R_1$-$R_{10}$ is D, or a pharmaceutically acceptable salt thereof,
for use in an amount of 0.2 mg-2 mg per day in treating an autoimmune disease in a human subject.

By any range disclosed herein, it is meant that all hundredth, tenth and integer unit amounts within the range are specifically disclosed as part of the invention. Thus, for example, 0.01 mg to 50 mg means that 0.02, 0.03 ... 0.09; 0.1, 0.2 ... 0.9; and 1, 2 ... 49 mg unit amounts are included as embodiments of this invention.

Deuterium (D or 2H) is a stable, non-radioactive isotope of hydrogen and has an atomic weight of 2.0144. Hydrogen atom in a compound naturally occurs as a mixture of the isotopes 1H (hydrogen or protium), D (2H or deuterium), and T (3H or tritium). The natural abundance of deuterium is 0.0156%. Thus, a compound with a level of deuterium at any site of hydrogen atom in the compound that has been enriched to be greater than its natural abundance of 0.0156%, is novel over non-enriched counterpart.

As used herein, a "deuterium-enriched" compound means that the abundance of deuterium at any relevant site of the compound is more than the abundance of deuterium naturally occurring at that site in an amount of the compound. A relevant site in a compound as used above is a site which would be designated as "H" in a chemical structure representation of the compound when not deuterium-enriched. Naturally occurring as used above refers to the abundance of deuterium which would be present at a relevant site in a compound if the compound was prepared without any affirmative step to enrich the abundance of deuterium. Thus, in a "deuterium-enriched" compound, the abundance of deuterium at any of its relevant sites can range from more than 0.0156% to 100%. Examples of ways to obtain a deuterium-enriched compound are exchanging hydrogen with deuterium or synthesizing the compound with deuterium-enriched starting materials.

Obtaining 100% deuteration at any relevant site of a compound in an amount of milligram or greater can be difficult. Therefore, it is understood that some percentage of hydrogen may still be present, even though a deuterium atom is specifically shown in a chemical structure. Thus, when a chemical structure contains a "D", the compound represented by the structure is deuterium-enriched at the site represented by "D".

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography, elemental analysis, Ames test, dissolution, stability and any other quality that can be determined by an analytical method. Once the characteristics of a compound are known, the information can be used to, for example, screen or test for the presence of the compound in a sample.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

As used herein, an "isolated" compound is a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to eliminate the presence of chemical entity in the composition.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R §211.166, the entire content of which is hereby incorporated by reference.

As used herein, "about" in the context of a numerical value or range means±10% of the numerical value or range recited or claimed.

Laquinimod is a small molecule having the following chemical structure:

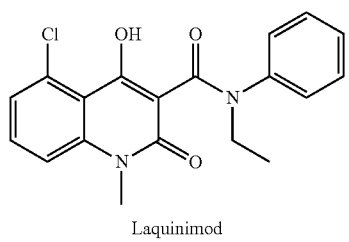 [SMILES: CCN(C(=O)c1c(O)c2c(Cl)cccc2n(C)c1=O)c1ccccc1]

Laquinimod

It is an oral immunomodulator which has demonstrated therapeutic effect in various experimental inflammatory/autoimmune animal models, such as Experimental Autoimmune Encephalomyelitis (EAE), an animal model for Multiple Sclerosis (MS), Dextran Sodium Sulphate (DSS) induced colitis for Inflammatory Bowel Disease, Non-Obese Diabetic (NOD) mice for Type I Diabetes (IDDM), Experimental Autoimmune Neuritis (EAN) for Guillain-Barre Syndrome, Systemic Lupus Erythematosus (SLE), lupus nephritis, lupus arthritis, Crohn's Disease and Rheumatoid arthritis. The therapeutic activity of laquinimod in these models results from a variety of mechanistic effects, including reduction of leukocyte infiltration into target tissues by modulation of chemokine-mediated T-cell adhesion, modulation of cytokine balance, down regulation of MHC class II resulting in alteration of antigen presentation, and effects on dendritic cells subpopulations.

A pharmaceutically acceptable salt of laquinimod, as well as of the deuterated compounds herein, includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, which are hereby incorporated by reference into this application.

A dosage unit may comprise a single compound or mixtures of compounds thereof. A dosage unit can be prepared for oral dosage forms, such as tablets, capsules, pills, powders, and granules.

Laquinimod, as well as of the deuterated compounds herein, can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit is preferably in a form suitable for oral administration. Laquinimod, as well as of the deuterated compounds herein, can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO 2007/146248.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

Metabolites from chemical compounds, whether inherent or pharmaceutical, are formed as part of the natural biochemical process of degrading and eliminating the compounds. The rate of degradation of a compound is an important determinant of the duration and intensity of its action. Profiling metabolites of pharmaceutical compounds, drug metabolism, is an important part of drug discovery, leading to an understanding of any undesirable side effects.

Metabolization of Laquinimod

Laquinimod has been shown to be slowly metabolized by CYP3A4 (Cytochrome P450 3A4) to form several minor metabolites and some of them may undergo further metabolism by Phase 2 metabolic reactions. See, e.g. Tuvesson et al. "Cytochrome P450 3A4 is the major enzyme responsible for the metabolism of laquinimod, a novel immunomodulator", Drug Metabolism and Disposition, Vol. 33, No. 6, pages 866-872. DELAQ (des-ethyl-laquinimod; 5-chloro-4-hydroxy-1-methyl-2-oxo-N-phenyl-1,2-dihydroquinoline-3-carboxamide), having the following chemical structure, is one of the oxidative metabolites of laquinimod.

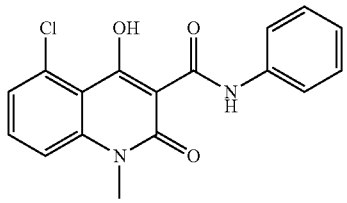 [SMILES: Cn1c(=O)c(C(=O)Nc2ccccc2)c(O)c2c(Cl)cccc21]

In addition, clinical data has shown that DELAQ levels in human body are at certain constant ratio to the laquinimod levels either in terms of Cmax or AUC. Such a behavior suggests that the formation of the metabolite, DELAQ, is PK "formation rate limited".

Described below are experiments showing that the deuterated form of laquinimod is more resistant to metabolic changes, especially those changes mediated by cytochrome P450 systems. Deuteration of the C—H bond to be oxidized may change the pathway of drug metabolism (metabolic switching). The metabolic scheme below illustrates slower CYP3A4-mediated DELAQ formation with deuterated laquinimod:

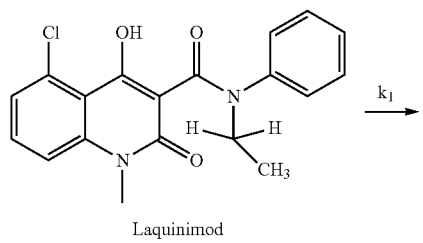
Laquinimod

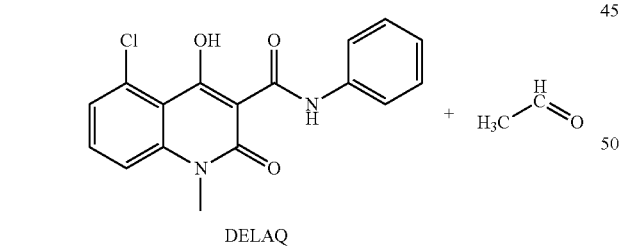
DELAQ

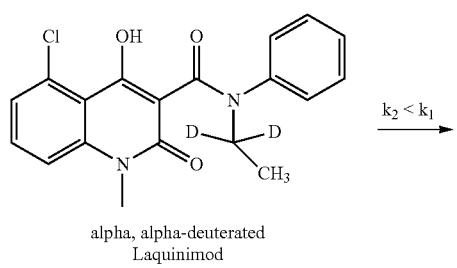
alpha, alpha-deuterated
Laquinimod

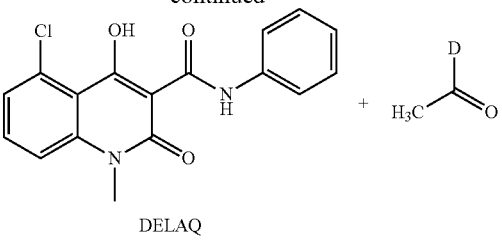
DELAQ

Deuteration of the phenyl moiety may affect position of the amide-bond relative to CYP catalytic center prior to oxidation of α-carbon of the ethyl group. This may explain why deuterated laquinimod with various deuteration at ethyl and/or phenyl moieties results in, for example, reduced formation of optionally deuterated DELAQ.

DELAQ as an Impurity

DELAQ is also an undesirable synthetic by-product of laquinimod synthesis. Any activity of DELAQ has not been fully characterized. It is also generally preferable to minimize the amount of an impurity in a drug substance and the final drug product.

DELAQ as an impurity in the laquinimod sodium drug substance is tested by a HPLC method and the specification for this impurity is provided as not more than 0.1%. The GMP drug substance batches of laquinimod sodium have been tested and the levels of DELAQ in these batches have been found to be less than 3 ppm. Similar parameters are therefore provided for drug product containing compounds of this invention.

Several analytical and bioanalytical methods were developed for determination of optionally deuterated DELAQ concentrations. The current bioanalytical methods for optionally deuterated DELAQ analysis in various matrices are based on LC-MS and have sensitivity at the low pg/mL plasma level.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Preparation of Deuterated Laquinimod

Step 1: Synthesis of Deuterated N-Ethyl-aniline

N-Ethyl-D5-aniline

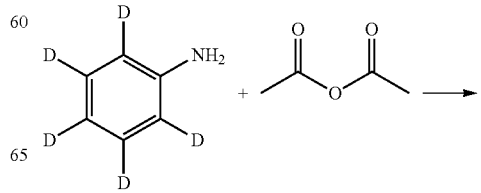

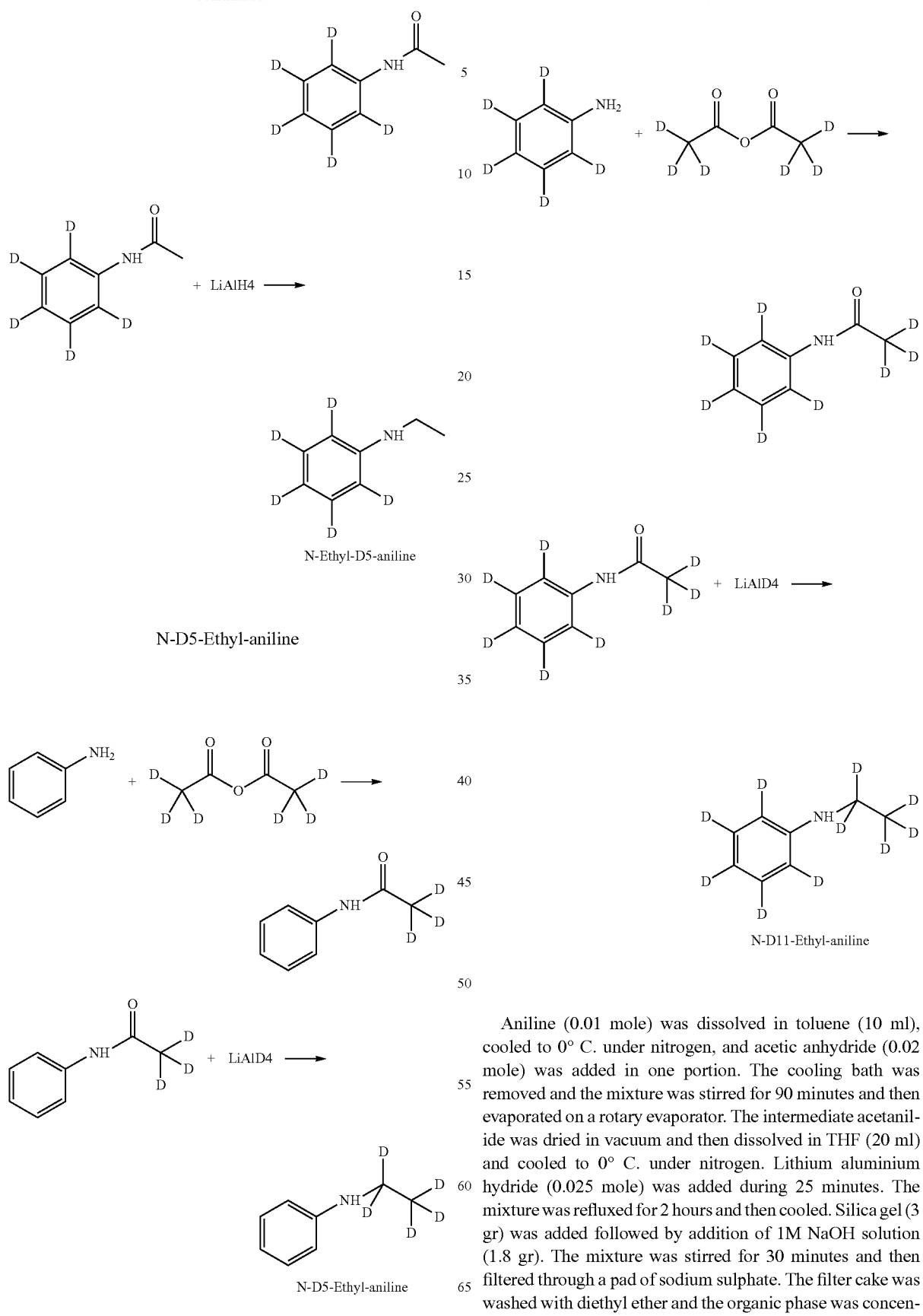

Aniline (0.01 mole) was dissolved in toluene (10 ml), cooled to 0° C. under nitrogen, and acetic anhydride (0.02 mole) was added in one portion. The cooling bath was removed and the mixture was stirred for 90 minutes and then evaporated on a rotary evaporator. The intermediate acetanilide was dried in vacuum and then dissolved in THF (20 ml) and cooled to 0° C. under nitrogen. Lithium aluminium hydride (0.025 mole) was added during 25 minutes. The mixture was refluxed for 2 hours and then cooled. Silica gel (3 gr) was added followed by addition of 1M NaOH solution (1.8 gr). The mixture was stirred for 30 minutes and then filtered through a pad of sodium sulphate. The filter cake was washed with diethyl ether and the organic phase was concentrated on a rotary evaporator to give the title compounds.

Step 2: Synthesis of Deuterated Laquinimod

N-ethyl-N-D5-phenyl-1,2-dihydro-4-hydroxy-5-chloro-1-methyl-2-oxoquinoline-3-carboxamide
(Compound 1)

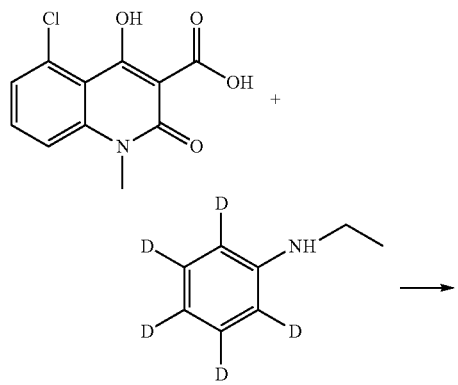

Compound 1

N-D5-ethyl-N-phenyl-1,2-dihydro-4-hydroxy-5-chloro-1-methyl-2-oxoquinoline-3-carboxamide
(Compound 2)

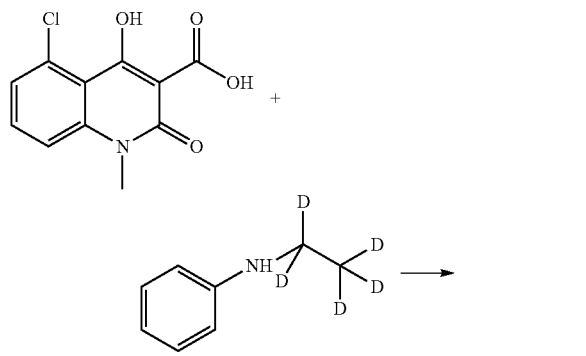

Compound 2

N-D5-ethyl-N-D5-phenyl-1,2-dihydro-4-hydroxy-5-chloro-1-methyl-2-oxoquinoline-3-carboxamide
(Compound 3)

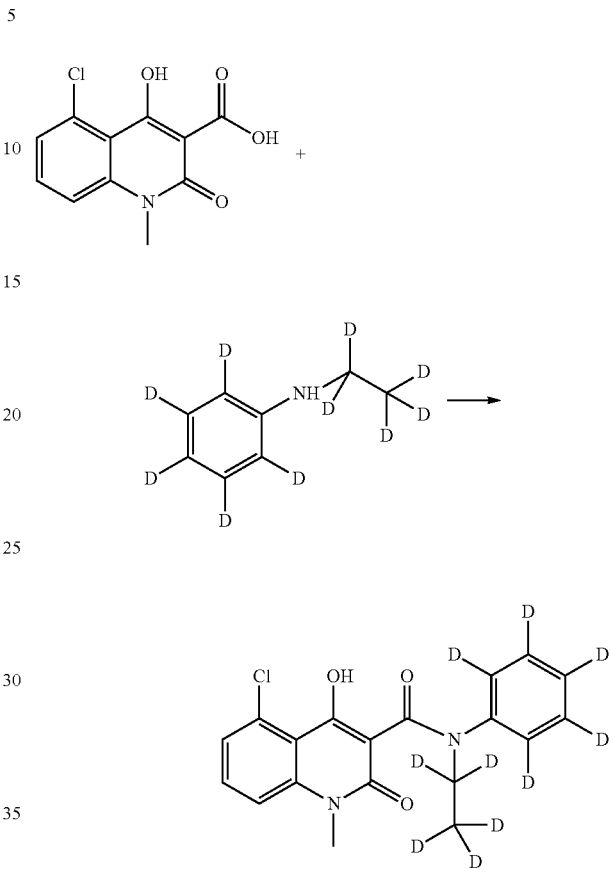

Compound 3

N-Ethyl-aniline (0.01 mole) and MCQCA(1,2-Dihydro-4-hydroxy-5-chloro-1-methyl-2-oxo-quinoline-3-carboxylic acid) (2.03 gr, 0.008 mole) were stirred in dichloromethane (32 ml) and triethylamine (4.2 ml) was added. The mixture was cooled in an ice/water bath under nitrogen and thionyl chloride (1.33 gr) was added dropwise during 30 minutes. The mixture was stirred at 0° C. for additional 3 hours and then extracted with cold aqueous 1M sulphuric acid. The organic phase was extracted with, 1M NaOH solution and the aqueous phase was concentrated a little on a rotary evaporator to remove traces of organic solvents. 5M HCl was added to pH 1-1.5 and the resulting suspension stirred for 30 minutes. The precipitated product was filtered, washed with water and dried in vacuum. Deuterated laquinimod was then obtained (86-93% yield).

Step 3: Preparation of Deuterated Laquinimod Sodium salt

Deuterated laquinimod prepared in Step 2 was suspended in ethanol and treated with 20% aqueous NaOH solution. The precipitated sodium salt was stirred for 3 hours, filtered and washed with ethanol. Drying in vacuum provided deuterated laquinimod sodium salt (92-94% yield). Identity and purity were proven by NMR, MS and HPLC.

Isotopic purity and assay of deuterated compounds 1-3

| Compound | Isotopic Purity (LC/MS/MS) | Assay |
|---|---|---|
| 1 | 100.0% | 94.0% |
| 2 | 100.0% | 95.4% |
| 3 | 100.0% | 95.6% |

Example 2

Analysis of DELAQ

DELAQ is formed as a metabolite in rodents as well as in human body upon administration of laquinimod. Several analytical and bioanalytical methods were developed for determination of DELAQ concentrations, as a representative metabolite. The current bioanalytical methods for DELAQ analysis in various matrices are based on LC-MS and have sensitivity at the low pg/mL plasma level.

The following conditions were used in the determination of DELAQ in human plasma. The plasma is purified by on-line SPE after precipitation with LUDOX AS-40 colloidal silica solution followed by the analysis with HPLC with MS/MS detection.

Condition 1:

| | |
|---|---|
| Apparatus | LC/MS/MS SCIEX, QTRAP4000 Shimadzu Prominence HPLC System Controller: Shimadzu CBM-20A Pumps: Pump A: Shimadzu LC-20AD Pump B: Shimadzu LC-20AD Pump C: Shimadzu LC-20AB Autosampler: Shimadzu SIL-20AC Column Oven: Shimadzu CTO-20AC |
| Data Acquisition System | Analyst 1.4.2 or higher version |
| Column for analysis with Online filter | Waters Symmetry Shield RP18, 3.5 µm, 2.1 × 100 mm, Javelin 0.2 µm filter (Thermo Electron Corp, No. 88200) or equivalent |
| Column for SPE | Phenomenex C18-E, 20 µm, 2 × 20 mm |
| Column temperature | 30° C. |
| Autosampler temperature: | 15° C. |
| Injection volume | 160 µL |
| Run time | ~7 min (including on-line SPE and analysis) |
| Split ratio | None |
| Mobile phase | Solution A: 0.01% TFA in Water Solution B: 0.01% TFA in MeOH |
| Rinse liquid 1 | 200 mM PCA in water |
| Rinse liquid 2 | Acetone |
| Pretreatment A (Pump A) | 0.01% TFA in Water |
| Pretreatment B (Pump B) | 0.01% TFA in MeOH |

Condition 2.

| | |
|---|---|
| Apparatus | LC/MS/MS SCIEX, QTRAP4000 Shimadzu Prominence HPLC System Controller: Shimadzu CBM-20A Pumps: Pump A: Shimadzu LC-20AD Pump B: Shimadzu LC-20AD Pump C: Shimadzu LC-20AB Autosampler: Shimadzu SIL-20AC Column Oven: Shimadzu CTO-20AC |
| Data Acquisition System | Analyst 1.4.2 or higher version |
| Column for analysis with Online filter | Waters Symmetry Shield RP18, 3.5 µm, 2.1 × 100 mm, Javelin 0.2 µm filter (Thermo Electron Corp, No. 88200) or equivalent |
| Column for SPE | Phenomenex C18-E, 20 □m, 2 × 20 mm |
| Column temperature | 30° C. |
| Autosampler temperature: | 15° C. |
| Injection volume | 80 µL |
| Run time | ~7 min (including on-line SPE and analysis) |
| Split ratio | None |
| Mobile phase | Solution A: 0.01% TFA in Water Solution B: 0.01% TFA in MeOH |
| Rinse liquid 1 | 200 mM PCA in water |
| Rinse liquid 2 | Acetone |
| Pretreatment A (Pump A) | 0.01% TFA in Water |
| Pretreatment B (Pump B) | 0.01% TFA in MeOH |

DELAQ in rat plasma was also determined under the following condition. The plasma was purified by on-line SPE after precipitation with LUDOX AS-40 colloidal silica solution followed by the analysis with HPLC with MS/MS detection.

Example 3

Pharmacokinetic and Partial Metabolic Evaluation

The main objectives of this example were:
Quantification of Compound 1, Compound 2, Compound 3 and Laquinimod in rat plasma using LC/MS/MS bioanalytical method.

Characterization of the pharmacokinetic profile of Compound 1, Compound 2, Compound 3 and Laquinimod following oral (PO) administration at a dose of 0.2 mg/kg.

The measurement DELAQ concentrations in the collected plasma samples.

The dose level selected in this example has been used in a pharmacological study previously conducted with laquinimod.

General Design

Rats cannulated at the right common jugular vein by polyethylene tubing were used. In the in-life part, three cannulated female rats were treated with each of the four test articles at dose of 0.2 mg/kg.

Blood was withdrawn from the rats at five different time points for the preparation of plasma. The concentrations of Compound 1, Compound 2, Compound 3, laquinimod, and DELAQ were determined in these plasma samples, using applicable LC/MS/MS methods.

Materials

Testing Compounds a.       N-ethyl-N-D5-phenyl-1,2-dihydro-4-hydroxy-5-chloro-1-methyl-2-oxoquinoline-3-carboxamide sodium salt (Compound 1) prepared in Example 1:
    Molecular weight: 383.8
    Appearance: White powder
    Storage: 2°-8° C., protected from light
    Purity: 100% purity was assumed.
    b.       N-D5-ethyl-N-phenyl-1,2-dihydro-4-hydroxy-5-chloro-1-methyl-2-oxoquinoline-3-carboxamide sodium salt (Compound 2) prepared in Example 1:
    Molecular weight: 383.8
    Appearance: White powder
    Storage: 2°-8° C., protected from light
    Purity: 100% purity was assumed.
    c.  N-D5-ethyl-N-D5-phenyl-1,2-dihydro-4-hydroxy-5-chloro-1-methyl-2-oxoquinoline-3-carboxamide sodium salt (Compound 3) prepared in Example 1:
    Molecular weight: 388.8
    Appearance: White powder
    Storage: 2°-8° C., protected from light
    Purity: 100% purity was assumed.
    d. Laquinimod sodium salt
    Molecular weight: 378.8
    Appearance: White powder
    Storage: Controlled room temperature (15°-25° C.), protected from light
    Assay by HPLC: 100.8%
    Purity: 100% purity was assumed.

Vehicle

Water, high purity (Direct Q, produced at the laboratory)

Other Materials

Isoflurane for anesthesia (FORANE®, ABBOTT)
    EDTA (Ethylenediaminetetraacetic acid disodium salt dihydrate, Sigma Aldrich, Product No: E4884-100 g)
    Heparin sodium salt, From Porcine Intestinal Mucosa, Sigma Aldrich, Product No: H9399-25KU)

Test System

Animal Specification

Species: rat
    Strain: SD (Sprague Dawley CD rats)
    Health status: SPF
    Age ordered: 8 weeks
    Number of animals: 20 cannulated females
    Weight range ordered: 200-225 g
    Acclimatization: at least 3 days
    At initiation of treatment:
    Number of animals: 12 cannulated females
    Approximate age: 9 weeks Justification of Selection of Test System The SD rat is a suitable rodent species and strain for pharmacokinetic studies and is acceptable to regulatory authorities. In addition, the pharmacokinetic profile of laquinimod in Sprague Dawley rats is well characterized.

Identification System

Each animal was identified by indelible marks on the body. The cages were marked with individual cards specifying strain, animal codes, group code, date and time of drug administration, test item and study code.

Specific Maintenance Schedule

Animal Housing Before and after Dose Administration

The animals were housed in an environmentally controlled room in group caging after the arrival to the facility. Rats were accommodated in individual polycarbonate or polysulphonate cages, with saw chips as matting for the floor.

Environmental Conditions

Controls were set to maintain temperature at 21±3° C. and relative humidity at 30-70%. A light/dark cycle of 12 hours light/12 hours dark were maintained automatically.

Drinking Water

Tap water filtered through a 0.2 μm filter was given ad libitum. The water was routinely analyzed (once every three months) for total microbial count, and for the absence of *Pseudomonas aeruginosa, Escherichia coli*, and *Clostridium* sps.

Feeding

Altromin VRF1 autoclaved food for rodents was provided ad libitum throughout the study. The diet was periodically analyzed.

Bedding

LIGNOCEL (SAWI, wood-shavings) autoclaved bedding was used. The quality of the bedding material is certified by the manufacturer.

No contaminants were known to be present in the diet, water or bedding at levels which might interfere with the study objectives.

Experimental Design

Acclimation

Each animal was inspected by qualified personnel, and patency of the cannula was verified by the ability to withdraw a blood sample upon animal receipt. Animals judged to be in good health were acclimated for at least 3 days. All animals received a detailed physical examination by the responsible veterinarian on the last day of acclimation period.

Randomization

After the acclimation period, animals judged to be in good health and suitable for testing were assigned to the study based on their body weight. At the randomization the body weights of the animals were within ±20% of the overall mean.

Organization of the Animal Dosage Level and Treatment Regimen

TABLE 1

Allocation of the cannulated animals to the experimental groups

| Group code | Dose volume [ml/kg] | Administration Test item [0.2 mg/kg*, PO] | Dose form [0.04 mg/ml*] | Group size/ Animal codes |
|---|---|---|---|---|
| Group 1C | 5 | Compound 1 | Compound 1 | 3/1-3 |
| Group 2C | 5 | Compound 2 | Compound 2 | 3/4-6 |

TABLE 1-continued

Allocation of the cannulated animals to the experimental groups

| Group code | Dose volume [ml/kg] | Administration Test item [0.2 mg/kg*, PO] | Dose form [0.04 mg/ml*] | Group size/ Animal codes |
|---|---|---|---|---|
| Group 3C | 5 | Compound 3 | Compound 3 | 3/7-9 |
| Group 4C | 5 | Laquinimod sodium | Laquinimod sodium | 3/10-12 |

*Dose is based on non-deuterated laquinimod free acid form.

The test item molecular weight ratio is 1.0757 for Compound 1 and Compound 2. The test item molecular weight ratio is 1.0898 for Compound 3. The test item molecular weight ratio is 1.0616 for Laquinimod sodium. These correction factors were applied to adjust the concentrations equivalent to non-deuterated laquinimod free acid.

Oral administration was performed by oral gavage at a dosage volume of 5 ml/kg using a blunt feeding stainless steel needle (Popper & Sons, USA). Body weights were measured before dose administration and doses were calculated on the basis of individual body weight.

Justification for Selection of Dose and Route of Administration

The dose level selected in this study has already been used in a pharmacological study previously conducted with laquinimod. The route of administration will be oral since it is the intended route of human exposure.

Preparation of Formulations and Measurement of Achieved Concentration

Preparation of Dosing Solutions

Appropriate amount of the test item was weighed and dissolved in water (vehicle) to achieve the required concentration, which was in each case equivalent to 0.04 mg/mL of non-deuterated laquinimod free acid.

Dissolution of the test items were achieved by gentle shaking, stirring, low speed vortex or a sonicator. No correction factor was applied to adjust for purity.

Storage and Stability of Formulations

All dosing solutions were stored at 2-8° C. in tightly closed amber glass containers, protected from light. Prior to use formulations were taken from the refrigerator, and then allowed to reach ambient room temperature (15-25° C.). Dosing solutions were assumed to be stable for at least 48 h, based on stability data of similar laquinimod dosing solutions.

Achieved Concentration for Dosing Solutions

Before treatment laquinimod concentrations in dosing solutions were determined by validated HPLC methods with UV detection in duplicate samples taken from solutions. The achieved concentrations were within ±10 % of the nominal concentrations.

Clinical Observation

Mortality, sign of illness or severe reaction to treatment was documented.

Blood Sampling, Plasma Preparation

Blood were withdrawn from animals at the following time points: 1, 2, 4, 8 and 24 hours after dosing as detailed in the table below. The actual sampling time were recorded.

TABLE 2

| | Time points or blood collection | | | | |
|---|---|---|---|---|---|
| Animal codes | 1 h | 2 h | 4 h | 8 h | 24 h |
| 1-12 | yes | yes | yes | yes | yes |

Blood Collection from Cannulated Rats

Each animal was restrained firmly. After the removal of the seal the port of the cannula was accessed with an appropriate blunted needle mounted on a syringe containing PBS. After having withdrawn approximately 100 μL of blood, the syringe was changed to a clean heparinized syringe. Approximately 250 μL of blood was collected for the preparation of plasma. The first 100 μL fraction of blood was returned and 250 μL of PBS was given to the animal through the catheter. The catheter was filled by heparinized glycerol (100 IU/ml) solution prepared by mixing 10 ml stock heparin (200 IU/ml) with 10 ml of sterile glycerol (d=1.26 g/mL). Blood specimens were mixed immediately and were placed on water ice.

Preparation of Plasma

Centrifugation was carried out as soon as practicable and not more than 40 minutes from collection.

Whole blood was centrifuged at 2500 g for 10 min at 4° C., and the separated plasma was transferred into pre-labeled polypropylene tubes and the tubes were frozen at −70° C. within 70 minutes of collection.

The frozen samples were transferred to Bioanalytical Laboratory for determination of laquinimod concentration where they were stored at nominal −70° C. until analysis.

Bioanalysis of Plasma Samples

The concentrations of test items (Compound 1, Compound 2, Compound 3 and Laquinimod) and the concentration of DELAQ were determined in the plasma samples by using reliable LC/MS/MS assay.

Pharmacokinetic Data Analysis

Pharmacokinetic parameters were calculated and the mean plasma levels versus time curves were evaluated.

The following pharmacokinetic parameters were determined from the mean plasma concentration-time data (mean of three animals at each time point) of Compound 1, Compound 2, Compound 3 and Laquinimod.

| Parameter | Definition |
|---|---|
| AUC(0-t) | Area under the plasma concentration-time curve from time zero up to time of last detectable concentration (tz) |
| AUC(0-∞) | Area under the plasma concentration-time curve from time zero up to infinity |
| Cmax | Maximum observed plasma concentration |
| tmax | Time of maximum observed plasma concentration |
| t1/2 | Apparent terminal elimination half-life |

Summary of the Results

Figure 2:
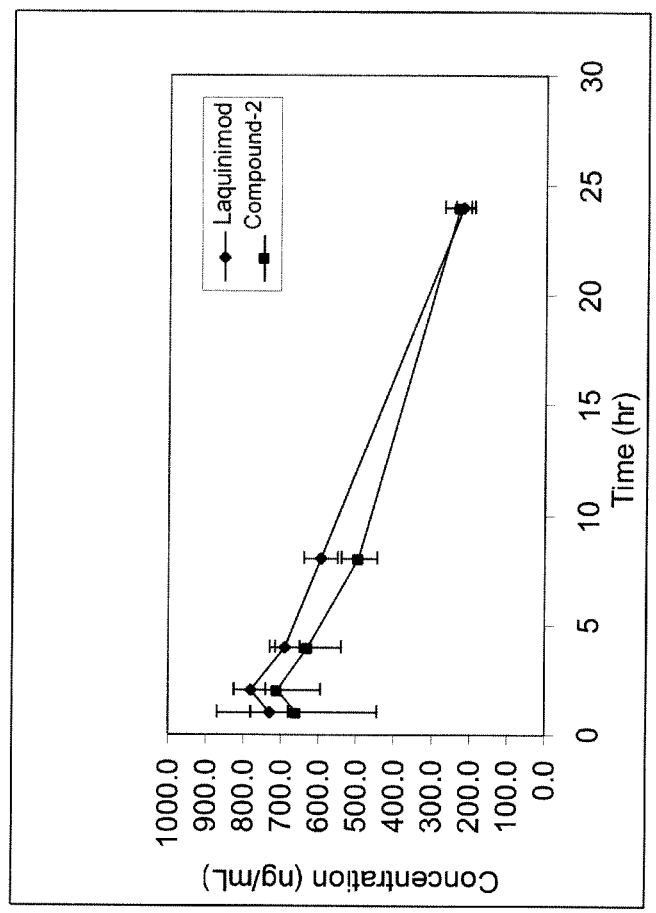
FIG. 2 shows the average plasma concentration-time profile for laquinimod vs. Compound 2 following oral administration to rats at 0.2 mg/kg.

As shown in Tables 3-6 below and in FIG. 2, the average plasma concentration of deuterium-enriched laquinimod is comparable to that of non-deuterium-enriched laquinimod.

The concentration-time profiles of the test items did not differ significantly. Maximal mean concentrations were reached by 1 or 2 hours after the administration, and varied between 703 and 798 ng/mL. The mean concentrations decreased to 194-227 ng/mL by 24 hours post dose. The AUC values for laquinimod, Compound 1, Compound 2 and Compound 3 were 15506.0, 13783.4, 12289.8 and 15750.2, respectively also indicating no significant difference in exposure.

TABLE 3

Individual and average PK parameters for laquinimod in rats following oral administration at 0.2 mg/kg

| PK Parameter | $C_{max}$ (ng/mL) | $T_{max}$ (hr) | $T_{1/2}$ (hr) | $AUC_{last}$ (hr*ng/mL) | $AUC_{inf}$ (hr*ng/mL) |
|---|---|---|---|---|---|
| Rat# 10 | 770.0 | 2.0 | 12.0 | 11013.8 | 14691.6 |
| Rat# 11 | 774.8 | 1.0 | 12.4 | 12659.7 | 17141.8 |
| Rat# 12 | 838.8 | 2.0 | 10.9 | 11487.3 | 14684.6 |
| Average | 794.5 | 1.7 | 11.8 | 11720.3 | 15506.0 |
| STDEV | 38.4 | 0.6 | 0.8 | 847.3 | 1416.6 |

TABLE 4

Individual and average PK parameters for Compound 1 in rats following oral administration at 0.2 mg/kg

| PK Parameter | $C_{max}$ (ng/mL) | $T_{max}$ (hr) | $T_{1/2}$ (hr) | $AUC_{last}$ (hr*ng/mL) | $AUC_{inf}$ (h*ng/mL) |
|---|---|---|---|---|---|
| Rat# 1 | 730.7 | 2.0 | 12.1 | 10011.7 | 13617.9 |
| Rat# 2 | 611.9 | 2.0 | 9.5 | 8039.3 | 9733.8 |
| Rat# 3 | 809.5 | 2.0 | 10.0 | 10061.6 | 12447.9 |
| Rat# 13 | 944.9 | 1.0 | 13.4 | 13681.5 | 19333.9 |
| Average | 774.3 | 1.8 | 11.3 | 10448.5 | 13783.4 |
| STDEV | 139.8 | 0.5 | 1.8 | 2352.1 | 4042.2 |

TABLE 5

Individual and average PK parameters for Compound 2 in rats following oral administration at 0.2 mg/kg

| PK Parameter | $C_{max}$ (ng/mL) | $T_{max}$ (hr) | $T_{1/2}$ (hr) | $AUC_{last}$ (hr*ng/mL) | $AUC_{inf}$ (hr*ng/mL) |
|---|---|---|---|---|---|
| Rat# 4 | 827.6 | 1.0 | 13.6 | 10422.1 | 14699.6 |
| Rat# 5 | 551.4 | 2.0 | 13.4 | 8741.6 | 12439.0 |
| Rat# 6 | 816.2 | 2.0 | 14.6 | 11975.3 | 11975.3 |
| Rat# 15 | 703.6 | 2.0 | 13.6 | 10045.4 | 10045.4 |
| Average | 724.7 | 1.8 | 13.8 | 10296.1 | 12289.8 |
| STDEV | 128.4 | 0.5 | 0.5 | 1331.0 | 1911.9 |

TABLE 6

Individual and average PK parameters for Compound 3 in rats following oral administration at 0.2 mg/kg

| PK Parameter | $C_{max}$ (ng/mL) | $T_{max}$ (hr) | $T_{1/2}$ (hr) | $AUC_{last}$ (hr*ng/mL) | $AUC_{inf}$ (hr*ng/mL) |
|---|---|---|---|---|---|
| Rat# 7 | 728.9 | 2.0 | 12.7 | 11280.4 | 15225.2 |
| Rat# 8 | 833.2 | 1.0 | 12.0 | 5317.8 | 14845.1 |
| Rat# 9 | 904.3 | 1.0 | 11.6 | 11156.0 | 14643.7 |
| Rat# 17 | 907.5 | 1.0 | 11.5 | 12110.0 | 15790.7 |
| Rat# 18 | 800.4 | 2.0 | 14.4 | 12471.5 | 18246.2 |
| Average | 834.9 | 1.4 | 12.4 | 10467.1 | 15750.2 |
| STDEV | 75.0 | 0.5 | 1.2 | 2931.2 | 1462.1 |

As shown in Tables 7 and 8 below and in FIG. 1, the amounts of DELAQ formed following oral administration of deuterium-enriched laquinimod is lower than the amount of DELAQ formed following administration of non-deuterium-enriched laquinimod. In average about ten-fold reduction could be observed in the DELAQ concentrations measured in the plasma of Compound 2 treated animals compared to the plasma of those that were treated with laquinimod. In the former group the mean DELAQ concentrations varied between 18.3 and 75.4 pg/mL, and in the group that received laquinimod it varied between 142 and 878 pg/mL. In both groups the lowest DELAQ concentration was measured at 1 hour following the administration and DELAQ concentrations increased until the last sample was taken at 24 hours post dose.

TABLE 7

Individual and average PK parameters for DELAQ formed from laquinimod in rats following oral administration at 0.2 mg/kg

| PK Parameter | $C_{max}$ (pg/mL) | $T_{max}$ (hr) | $AUC_{last}$ (hr*pg/mL) |
|---|---|---|---|
| Rat# 10 | 654 | 24 | 10369.0 |
| Rat# 11 | 1123 | 24 | 14606.5 |
| Rat# 12 | 858 | 24 | 13266.5 |
| Average | 878.3 | 24 | 12747.3 |
| STDEV | 235.2 | 0 | 2165.9 |

TABLE 8

Individual and average PK parameters for DELAQ formed from Compound 2 in rats following oral administration at 0.2 mg/kg

| PK Parameter | $C_{max}$ (pg/mL) | $T_{max}$ (hr) | $AUC_{last}$ (hr*pg/mL) |
|---|---|---|---|
| Rat# 4 | 62.0 | 24 | 1106.0 |
| Rat# 5 | 82.5 | 24 | 1065.3 |
| Rat# 6 | 77.3 | 24 | 1125.5 |
| Rat# 15 | 79.9 | 24 | 1318.8 |
| Average | 75.4 | 24 | 1153.9 |
| STDEV | 9.2 | 0 | 112.8 |

The testing results show that deuterium-enriched laquinimod reduces the formation of DELAQ, while maintaining a similar plasma concentration-time profile to that of non-deuterated laquinimod.

Example 4

Assessment of Efficacy of Deuterated Laquinimod (Compounds 1, 2 and 3) in MOG-Induced (Myelin-Oligodendrocyte-Glycoprotein) EAE (Experimental Autoimmune Encephalomyelitis)

The aim of this study was to assess the efficacy of three deuterated forms of laquinimod, compounds 1, 2 and 3, in comparison to laquinimod, using the MOG induced EAE in C57BL/6 mice.

EAE is an accepted animal model for multiple sclerosis, and induction with MOG in C57BL/6 is a well established model.

General Design

Disease was induced in the mice by the injection of the encephalitogenic emulsion.

Compounds 1, 2 and 3 at 10 mg/kg, laquinimod at 10 and 25 mg/kg or the vehicle were administered from study initiation (Day 0) until termination (Day 30). All the groups were treated orally, daily.

Materials:

Compounds 1, 2 and 3 were prepared as described in Example 1. laquinimod, manufactured in Teva.
Purified water (Direct-Q, Millipore).
Pertussis toxin: Sigma, Code # 2980, lot 044K1449.
MOG 35-55: Mnf Novatide, lot # 90016-71-1.
Complete Freund's Adjuvant (CFA): Sigma, code: F-5881, lot 104K8930.

Saline: Mnf-DEMO S.A, Code 05029, lot # 0101610.
*Mycobacterium tuberculosis* H37 RA (MT): Mnf-Difco.
Species, Strain and Supplier Healthy, nulliparous, non-pregnant female mice of the C57BL/6 strain obtained from Harlan Animal Breeding Center, Israel on 26.01.2010 were used in the study. The animals weighed 15-22 g, and were approximately 7-8 weeks old on arrival. The body weights of the animals were recorded on the day of delivery. Overtly healthy animals were assigned to study groups arbitrarily before treatment commenced. The mice were individually identified by using ear tags. A color-coded card on each cage gave information including cage number, group number and identification. Animals housing and care conditions were maintained.

EAE Induction

EAE was induced by injecting the encephalitogenic mixture (emulsion) consisting of MOG (150.0 μg/mouse) and CFA enriched with *M. tuberculosis* (1 mg/mL CFA).

A volume of 0.2 ml of emulsion was injected subcutaneously into the flanks of the mice.

Pertussis toxin was injected intraperitoneally on the day of induction and 48 hours later (total amount was 0.1+0.1=0.200 μg/mouse in 0.2 ml dosage volume).

The mice were allocated to 6 treatment groups: Vehicle, laquinimod (25 mg/kg and 10 mg/kg), and Compounds 1, 2 and 3, each 10 mg/kg.

Preparation and Administration of Encephalitogenic Emulsion

Oil portion: CFA (containing 1 mg/ml MT)

Liquid portion: 15.0 mg MOG was diluted in 10.0 ml Normal Saline to yield 1.5 mg/ml MOG stock solution. The emulsion was made from equal parts of oil and liquid portions (1:1) in two syringes connected to each other with a Leur lock, transferred to insulin syringe and 0.2 ml was injected to the right flank of each mouse.

Preparation and Administration of Pertussis Toxin

55 μL Pertussis toxin (200 μg/ml) was added to 21.945 ml saline to yield 500 ng/ml. The pertussis toxin was administered intraperitoneally on the day of encephalitogen injection and 48 hours later (100.0 ng/0.2 ml/mouse×2=200.0 ng/mouse).

Preparation and Administration of the Test Formulations

A concentration of 2.5 mg/ml laquinimod was prepared in purified water for dose level 25.0 mg/kg. The test formulation was stored at 2 to 8° C. until use in amber colored bottles. The mice of the 25 mg/kg laquinimod group were administered with the laquinimod at volume dose level of 200 μl/mouse by oral gavage, once daily (as shown in Table 4b).

A concentration of 1.0 mg/ml laquinimod was prepared in purified water for conventional laquinimod or Compounds 1, 2 and 3 for dose level 10.0 mg/kg. The test formulations were stored at 2 to 8° C. in amber colored bottles until use.

The mice were administered with the conventional laquinimod at volume dose level of 200 μl/mouse by oral gavage to the laquinimod 10 mg/kg group once daily. Administration of test compounds was performed in a similar fashion. The vehicle (double distilled water) was administered to the negative control group (Group # 1) in a similar manner.

Morbidity and Mortality

All animals were examined once daily to detect if any are moribund. Mice were weighed once weekly.

EAE Clinical Signs

The mice were observed daily from the 10th day post-EAE induction and EAE clinical signs were scored. The scores were recorded on observation cards according to the grades described in Table 4a below.

TABLE 4a

Evaluation of the EAE clinical signs

| Score | Signs | Description |
|---|---|---|
| 0 | Normal behavior | No neurological signs. |
| 1 | Limp tail | Part or the whole tail is limp and droopy. |
| 2 | righting reflex | Animal has difficulties rolling onto his feet when laid on its back |
| 3 | Hind leg weakness | wobbly walk - when the mouse walks the hind legs are unsteady |
| 4 | Hind leg paralysis | The mouse drags its hind legs but is able to move around using its fore legs |
| 5 | Full paralysis | The mouse can't move around, it looks thinner and emaciated. |
| 6 | Moribund/Death | |

All mice with score 1 and above were considered sick. When the first clinical sign appears all mice were given food soaked in water, which was spread on different places on the bedding of the cages. For calculation purposes, the score of animals that were sacrificed or died (6) was carried forward.

Interpretation of Results

Calculation of the Incidence of Disease (Disease Ratio)

The number of sick animals in each group were summed. The incidence of disease was calculated as $$\text{INCIDENCE of DISEASE} = \left(\frac{\text{No. of sick mice in treated group}}{\text{No. of sick mice in control group}}\right)$$

The percent inhibition according to incidence was calculated as $$\text{INHIBITION(\%) of INCIDENCE} = \left(1 - \frac{\text{Number of sick mice in treated group}}{\text{Number of sick mice in control group}}\right) \times 100$$

Calculation of the Mortality/Moribundity Rate (Mortality Ratio)

The number of dead or moribund animals in each group were summed. The mortality of disease was calculated as $$\text{MORTALITY of DISEASE} = \left(\frac{\text{No. of dead or moribund mice in treated group}}{\text{No. of dead or moribund mice in control group}}\right)$$

The percent inhibition according to mortality was calculated as $$\text{INHIBITION (\%) of MORTALITY} = \left(1 - \frac{\text{Number of dead or moribund mice in treated group}}{\text{Number of dead or moribund mice in control group}}\right) \times 100$$

Calculation of Duration of Disease

The mean duration of disease expressed in days was calculated as $$\text{Mean Duration} = \left(\frac{\sum \text{Duration of disease of each mouse}}{\text{No. of mice in the group}}\right)$$

Calculation of Mean Delay in Onset of Disease

The mean onset of disease expressed in days was calculated as $$\text{Mean Onset} = \left(\frac{\sum \text{Onset of disease of each mouse}}{\text{No. of mice in the group}}\right)$$

The mean delay in onset of disease expressed in days was calculated by subtracting the mean onset of disease in control group from test group.

Calculation of the mean maximal score and percent inhibition The mean maximal score (MMS) of each group was calculated as $$MMS = \left(\frac{\sum \text{Maximal Score of each mouse}}{\text{No. of mice in the group}}\right)$$

The percent inhibition according to MMS was calculated as $$\text{INHIBITION (\%) of } MMS = \left(1 - \frac{MMS \text{ of treated group}}{MMS \text{ of control group}}\right) \times 100$$

Calculation of the group mean score and percent inhibition The daily scores of each mouse in the test group were summed and the individual mean daily score (IMS) was calculated as $$IMS = \left(\frac{\sum \text{Daily score of mouse}}{\text{Observation period (days)}}\right)$$

The mean group score (GMS) was calculated as $$GMS = \left(\frac{\sum IMS \text{ of each mouse}}{\text{No. of mice in the group}}\right)$$

The percent inhibition was calculated as $$\text{INHIBITION (\%) of } GMS = \left(1 - \frac{GMS \text{ of treated group}}{GMS \text{ of control group}}\right) \times 100$$

A summary of the incidence, mortality, MMS, GMS, duration of the disease, onset of the disease and the activity of each group is shown in Table 4b below.

TABLE 4b

Mortality, incidence, MMS, GMS, Duration and Onset of EAE activity compared to vehicle

| Treatment | Mortality | Incidence | % inhibition 1 | MMS value | % inhibition 2 | GMS value | % inhibition 3 | Mean Duration (days) | Mean Onset (days) |
|---|---|---|---|---|---|---|---|---|---|
| Vehicle Water | 0/15 | 14/15 | — | 3.2 ± 1.3 | — | 2.21 ± 0.98 | — | 19.1 ± 5.5 | 11.9 ± 5.5 |
| laquinimod (25 mg/kg) | 0/15 | 4/15 | 71.4% | 1.3 ± 1.8 | 59.4% ($p < 0.001$) | 0.5 ± 0.13 | 97.7% ($p < 0.001$) | 3.0 ± 5.8 ($p < 0.001$) | 28.0 ± 5.8 ($p < 0.001$) |
| Laguinimod (10 mg/kg) | 0/15 | 9/15 | 35.7% | 2.1 ± 1.9 | 34.4% ($p = 0.17$) | 1.14 ± 0.5 | 48.4% ($p = 0.01$) | 9.3 ± 8.3 ($p < 0.001$) | 21.6 ± 8.4 ($p < 0.001$) |
| Compound 2 (10 mg/kg) | 0/15 | 13/15 | 7.1% | 2.1 ± 1.3 | 34.4% ($p = 0.02$) | 0.79 ± 0.2 | 64.3% ($p = 0.001$) | 13.2 ± 7.7 ($p = 0.004$) | 15.3 ± 6.8 ($p = 0.01$) |
| Compound 3 (10 mg/kg) | 0/15 | 10/15 | 28.6% | 1.6 ± 1.6 | 50.1% ($p = 0.01$) | 0.89 ± 0.94 | 59.7% ($p = 0.001$) | 9.6 ± 9.4 ($p = 0.001$) | 21.5 ± 9.3 ($p < 0.001$) |
| Compound 1 (10 mg/kg) | 0/15 | 8/15 | 42.9% | 1.5 ± 1.7 | 53.1% ($p = 0.01$) | 0.74 ± 0.86 | 66.5% ($p < 0.001$) | 7.9 ± 8.2 (<0.001) | 22.1 ± 8.9 ($p < 0.001$) |

Incidence and Mortality

14/15 mice were sick due to EAE in the vehicle treated control group. In the group treated with laquinimod (10 mg/kg), 9/15 mice were sick compared to 13/15, 10/15, and 8/15 in groups treated with compounds 2, 3 and 1 respectively. 4/15 mice were sick in the positive control group treated with 25 mg/kg laquinimod. No mortality was observed in any of the treatment groups.

There was a delay in the appearance of clinical signs in all groups treated with laquinimod (10 mg/kg) with onset between 15.3 and 22.1 days compared to control group (onset 11.9±5.5 days). The duration of EAE clinical signs in these treatment groups compared to the vehicle treated control group was between 7.9 and 13.2 days compared to 19.1±5.5 days in control group.

Mean Maximal Score (MMS) and Group Mean Score (GMS)

The MMS and GMS of the vehicle treated negative control group were 3.2±1.3 and 2.2±1.0, respectively. The positive laquinimod (25 mg/kg) control group exhibited 59.4% and 97.7% inhibition of EAE according to MMS (score 1.3±1.8) and GMS (score 0.5±0.1), respectively.

When the groups treated with Compound 1, 2 and 3 were compared to laquinimod, no significant difference in activity was observed. However there was a trend that showed that groups treated with Compound 1, 2 and 3 were more active than the laquinimod groups.

Figure 3:
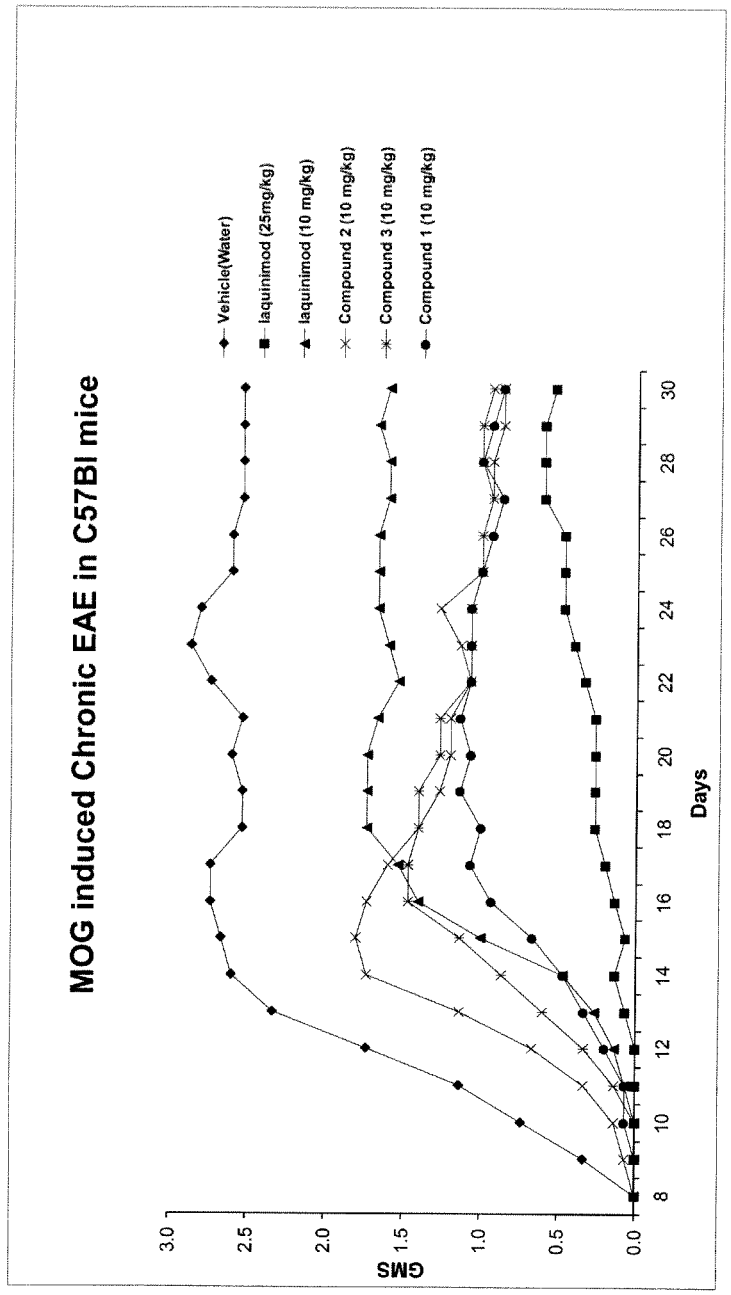
FIG. 3 shows Group Mean Score comparison in MOG induced SAE in mice treated with two doses of laquinimod and with Compound 1, 2 and 3 in various doses.

As shown in FIG. 3, on GMS scale, the laquinimod (10 mg/kg) group exhibited 48.4% activity compared to 64.3%, 59.7% and 66.5% activity in groups treated with Compound 2, 3 and 1 respectively.

Discussions

The testing results show that deuterium-enriched laquinimod reduces the formation of metabolites, in particular optionally deuterated DELAQ, while maintaining a similar plasma concentration-time profile to that of non-deuterated laquinimod.

The testing results also show that deuterium-enriched laquinimod are as active as or better than laquinimod in the inhibition of EAE clinical signs. The results of the study permit developing dosing parameters for deuterium-enriched laquinimod.

Example 5

In Vitro Evaluation of Laquinimod and Compound 2 as Inducers of Cytochrome P450 Expression in Cultured Human Hepatocytes 1. Introduction The objective of this study was to investigate the effects of treating primary cultures of fresh human hepatocytes with laquinimod or Compound 2 on the expression of CYP enzymes.

Cultured hepatocytes have proven to be a reliable test system for evaluating the inductive effects of NCEs. Hepatocytes can be isolated from non-transplantable human livers (Bjornsson et al., (2003), The conduct of in vitro and in vivo drug-drug interaction studies: a Pharmaceutical Research and Manufacturers of America (PhRMA) perspective. *Drug Metab Dispos* 31:815-832; Mudra and Parkinson, (2001), Preparation of hepatocytes, in *Current Protocols in Toxicology, Volume* 2 (Maines MD ed) unit 14.2, 13 p, John Wiley and Sons, Inc., New York, N.Y.) and cultured in a confluent monolayer (LeCluyse et al., (1994), Formation of extensive canalicular networks by rat hepatocytes cultured in collagen-sandwich configuration. *Am J Physiol* 266 (Cell Physiol. 35): C1764-C1774). After two to three days in culture, these cells regain their morphological integrity, and treatment with prototypical inducers results in the induction of appropriate CYP enzymes (LeCluyse et al., (1996), Cultured rat hepatocytes, in Pharmaceutical Biotechnology. Vol. 8, *Models for Assessing Drug Absorption and Metabolism*. (Borchardt R T, Wilson G and Smith P ads) pp 121-159, Plenum Press, New York; Robertson et al., (2000), In vitro inhibition and induction of human hepatic cytochrome P450 enzymes by modafinil. *Drug Metab Dispos* 28:664-671; Madan at al., (2003), Effects of prototypical microsomal enzyme inducers on cytochrome P450 expression in cultured human hepatocytes. *Drug Metab Dispos* 31:421-431). For this reason, it is acceptable to use cultured human hepatocytes to determine the potential of NCEs to cause induction of CYP enzymes.

This study was designed to allow any inductive effects of the test articles to be classified relative to two mechanistically distinct and clinically relevant CYP inducers, namely omeprazole (an AhR activator and CYP1A2 inducer) and rifampin (a PXR agonist and inducer of CYP3A4) (Parkinson and Ogilvie, (2008), Biotransformation of xenobiotics, in *Casarett & Doull's Toxicology, The Basic Science of Poisons. Seventh Edition*, (Klaassen CD ed) pp 161-304, The McGraw Hill Companies, Inc., New York). To this end, one preparation of cultured human hepatocytes from one liver was treated once daily for three consecutive days with DMSO (0.1% v/v, vehicle control), one of five concentrations of laquinimod (0.01, 0.05, 0.1, 1 or 10 µM) or Compound 2 (0.01, 0.05, 0.1, or 10 µM).

After treatment, the cells were incubated in situ with marker substrates for the analysis of phenacetin O-dealkylation (marker for CYP1A2) and midazolam 1'-hydroxylation (marker for CYP3A4/5) by LC/MS/MS. Following the in situ incubation, the same hepatocytes from the same treatment groups were harvested with TRIzol to isolate RNA, which was analyzed by qRT-PCR to assess the effect of laquinimod and Compound 2 on CYP1A2 and CYP3A4 mRNA levels. The study design, the test system and the selection and concentration of probe substrates used in this study were based on recommendations in the FDA's Draft Guidance Document on Drug Interaction Studies-Study Design, Data Analysis, and Implications for Dosing and Labeling and current FDA review articles (Food and Drug Administration, (2006), Draft Guidance for Industry: Drug Interaction Studies—Study Design, Data Analysis, and Implications for Dosing and Labeling, pp 55, U.S. Department of Health and Human Services, Rockville, Md.; Huang et al., (2008), New Era in Drug Interactions Evaluation: US Food and Drug Administration Update on CYP Enzymes, Transporters, and the Guidance Process. *J Clin Pharmacol* 48: 662-670; Zhang et al., (2009), Predicting Drug-Drug Interactions: An FDA Perspective. *The AAPS Journal* 11:300-306) and the PhRMA perspective on enzyme induction (Chu et al., (2009), In vitro and in vivo induction of cytochrome P450: a survey of the current practices and recommendations: a Pharmaceutical Research and Manufacturers of America (PhRMA) perspectice. *Drug Metab Dispos* 27029 (87 pp) doi: 10.1124/dmd.109.0270).

2. Materials And Methods 2.1 Materials 2.1.1 Enzyme Activity Assays

| Enzyme | Reagent use | Name | Manufacturer |
|---|---|---|---|
| CYP1A2 | Substrate | Phenacetin | Sigma-Aldrich |
| | Substrate metabolite | Acetaminophen | Sigma-Aldrich |
| | Internal standard | Acetaminophen-$d_4$ | Proprietary information |
| CYP3A4/5 | Substrate | Midazolam | Sigma-Aldrich |
| | Substrate metabolite | 1'-Hydroxymidazolam | Cerilliant |
| | Internal standard | 1'-Hydroxymidazolam-$d_4$ | Proprietary information |

2.1.2 Other Assays

| Assay | Name | Manufacturer |
|---|---|---|
| qRT-PCR | RNase-free water | Fisher Scientific |
| qRT-PCR | High-capacity cDNA reverse transcription kit with RNase-inhibitor | Applied Biosystems |
| qRT-PCR | TaqMan universal master mix | Applied Biosystems |
| qRT-PCR | TaqMan gene expression assays | Applied Biosystems |
| qRT-PCR | TRIzol reagent | Invitrogen |
| qRT-PCR | Chloroform | Fisher Scientific |
| qRT-PCR | 2-Propanol | Fisher Scientific |
| qRT-PCR | Ethanol, 200 proof | Sigma-Aldrich |
| qRT-PCR | 1X tris-EDTA, pH 8.0 | Ambion |
| qRT-PCR | RNeasy mini kit | Qiagen |
| qRT-PCR | RNase-free DNase set | Qiagen |
| qRT-PCR | Proteinase K | Qiagen |
| qRT-PCR | RNA 6000 Nano LabChip kit | Agilent Technologies |

2.1.3 Other Reagents

| Name | Manufacturer |
| --- | --- |
| Acetonitrile | Fisher Scientific |
| Ammonium acetate | Sigma-Aldrich |
| Carbon dioxide | Helget Gas |
| Dexamethasone | Sigma-Aldrich |
| DMSO | Sigma-Aldrich |
| EDTA | Sigma-Aldrich |
| Ethanol | Fisher Scientific |
| Formic acid | EM Science |
| ITS+ | BD Biosciences |
| L-Arginine | Sigma-Aldrich |
| L-Glutamine | Sigma-Aldrich |
| Magnesium cholride | Sigma-Aldrich |
| Methanol | Fisher Scientific |
| Methylene chloride (dichloromethane) | Sigma-Aldrich |
| Mibefradil | Sigma-Aldrich |
| Modified Eagle Medium (MCM) (Dr. Chee's Modification) | Invitrogen |
| Omeprazole | Sigma-Aldrich |
| Penicillin-Streptomycin (Pen-Strep) | Invitrogen |
| Potassium hydroxide | Fisher Scientific or Gentest |
| Potassium phosphate (monobasic and dibasic) | Mallinckrodt Baker |
| Rifampin | Sigma-Aldrich |
| Sodium bicarbonate | Sigma-Aldrich |
| Sodium carbonate | Fisher Scientific |
| Sodium chloride solution (endotoxin tested) | Sigma-Aldrich |
| Sodium hydroxide | Fisher Scientific |
| Sterile high purity water | XenoTech |
| Sucrose | Sigma-Aldrich |
| Thymidine | Sigma-Aldrich |
| Tris | Sigma-Aldrich |

2.2 Test System

One preparation of freshly isolated human hepatocytes (hereafter, referred to as H971) supplied by XenoTech, LLC at 16825 West 116$^{th}$ Street, Lenexa, Kans. 66219, was treated in this study.

2.2.1 Treatment of Cultured Human Hepatocytes

Hepatocyte cultures were treated daily for three consecutive days and cultured according to SOP L5021.01 (Xeno-Tech, LLC) and previously described methods (Robertson et al., (2000), In vitro inhibition and induction of human hepatic cytochrome P450 enzymes by modafinil. *Drug Metab Dispos* 28:664-671; Madan et al., (2003), Effects of prototypical microsomal enzyme inducers on cytochrome P450 expression in cultured human hepatocytes. *Drug Metab Dispos* 31:421-431; Paris et al., (2009), In vitro inhibition and induction of human liver cytochrome P450 (CYP) enzymes by milnacipran. *Drug Metab Dispos* 37:2045-2054). Cultures were treated with supplemented MOM each well was treated with 0.2 mL) containing 0.1% DMSO (vehicle, negative control), one of five concentrations of laquinimod (0.01, 0.05, 0.1, 1 or 10 µM) or Compound 2 (0.01, 0.05, 0.1, 1 or 10 µM), mibefradil (10 µM) or one of two known human CYP enzyme inducers, namely, omeprazole (100 µM) and rifampin (10 µM), positive controls.

2.2.2 RNA Isolation from Cultured Human Hepatocytes, Purification and Quantification Approximately 24 hours after the last treatment, hepatocytes were lysed in TRIzol reagent after the in situ marker substrate incubations, and cell lysates were stored at −75±5° C. For human hepatocyte preparation H971, media from six wells per treatment group was aspirated, and approximately 132 µL TRIzol were added to each well. The cell lysates were mixed by repeated pipetting. Total RNA was isolated from the cell lysates using the TRIzol protocol (Invitrogen) and was purified using the RNeasy Mini Kit (Qiagen Inc.) according to SOP L6161.02. RNA quality and concentration were determined by measuring absorbance at 260 and 280 nm on a BioTek Synergy HT plate reader (BioTek Instruments, Inc.) with KC4 Signature software (version 3.4 Rev 21, BioTek Instruments, Inc.) according to SOP L6162.02. The analysis of RNA integrity was carried out with the RNA 6000 Nano Assay Kit on an Agilent 2100 Bioanalyzer (Agilent Technologies, Inc.) according to SOP L6162.02. Single-stranded cDNA was prepared from RNA with the RT Master Mix using the AB 7300 Real Time PCR system thermocycling program or AB 7900HT Fast Real Time PCR System thermocycling program (Applied Biosystems) according to SOP L6160.04. The RT Master Mix is comprised of 10×RT buffer, 25× deoxyNTPs, 10× Random hexamers, RNase Inhibitor (20 U/µL), MultiScribe reverse transcriptase (50 U/µL) and RNase-free water. The RT Master Mix was added to each RNA sample to complete the components of the reaction. No template controls (NTCs) were included in the analysis. For the NTC reactions, RNase-free water was added in place of the RNA sample. The cDNA prepared samples were stored at −20±5° C. prior to analysis by qRT-PCR.

2.3 Test Articles

Laquinimod sodium was prepared according to the procedures described in U.S. Pat. No. 6,077,851 and Compound 2 was prepared according to the procedures described in Example 1.

| | Laquinimod | Compound 2 |
| --- | --- | --- |
| Storage of test article: | Locked storage at 2 to 8° C.), protected from light and moisture | Locked storage at 2 to 8° C.), protected from light and moisture |
| Quantity received: | 53.09 mg | 50.58 mg |
| Molecular mass: | 378.78 g/mol (sodium salt) 356.80 g/mol (free acid) | 383 g/mol |
| Purity: | 100% | 95.4% |
| Appearance: | White powder | Pale yellow |
| Solvent used for dissolution: | High purity sterile water | High purity sterile water |
| Concentration of stock solutions: | 0.01, 0.05, 0.1, 1, 2, 10 and 20 mM | 0.01, 0.05, 0.1, 1 and 10 mM |
| Concentration of working solutions: | 0.01, 0.05, 0.1, 1, 2, 10 and 20 µM (stock diluted in supplemented MCM medium; final concentration of DMSO in culture medium = 0.1% v/v) | 0.01, 0.05, 0.1, 1 and 10 µM (stock diluted in supplemented MCM medium; final concentration of DMSO in culture medium = 0.1% v/v) |
| Storage of stock solutions: | −20 ± 5° C. | −20 ± 5° C. |

A solution of laquinimod or Compound 2 (10 mM in high purity sterile water) was prepared by dissolving the appropriate amount of either laquinimod or Compound 2 in high purity sterile water. For laquinimod, the 10 mM stock solution was diluted with high purity sterile water to 2, 1 and 0.1 µM. Furthermore, the 1 µM solution was diluted with high purity sterile water to 0.05 and 0.01 mM. For Compound 2, the 10 mM stock solution was then diluted with high purity sterile water to 1 and 0.1 µM. Furthermore, the 1 µM solution was diluted with high purity sterile water to 0.05 and 0.01 mM. The solutions of laquinimod and Compound 2 (all mM concentrations) were divided into a sufficient number of aliquots to be used individually in the study and were protected from light with amber glassware or aluminum foil and stored frozen (−20±5° C.) with a two month expiration date.

Prior to treatment each day, an aliquot of the laquinimod and Compound 2 stock solutions were conditioned to room temperature and gently shaken or vortexed on a low setting. Stock solutions of laquinimod (0.01, 0.05, 0.1, 1 and 10 mM) and Compound 2 (0.01, 0.05, 0.1, 1 and 10 mM) were then diluted in cell culture media (1:1000 dilution) and the resulting working dose solution was added to the hepatocyte cultures to give the final concentrations of laquinimod (0.01, 0.05, 0.1, 1 and 10 µM) and Compound 2 (0.01, 0.05, 0.1, 1 and 10 µM) within two hours of dilution (approximately 15 minutes to 65 minutes). A qualitative visual examination of the stock and dosing solutions was conducted prior to application to the hepatocytes in order to determine solubility in the test system.

Just prior to treatment, on each day of treatment, and just prior to incubation of the marker substrates, spent culture medium (spent dosing media) were collected from the vehicle, laquinimod and Compound 2 treatment groups. Approximately 150 µL was collected from each of three wells, from each aforementioned treatment groups, and pooled for each sample to a final volume of approximately 450 µL. These spent media samples were analyzed for residual laquinimod, Compound 2 and the de-ethylated metabolite (DELAQ).

2.4 Positive Controls and Vehicle

The following chemicals or vehicles were used for dosing hepatocytes.

Omeprazole and rifampin and were dissolved in DMSO such that the final concentration of DMSO in the culture medium was 0.1% v/v. Mibefradil was prepared in high sterile purity water. According to SOP L5021.01 (XenoTech, LLC), working solutions of vehicle and positive controls were prepared fresh from the stock solution less than two hours prior to treatment on each treatment day (approximately 15 minutes to 65 minutes).

2.5 Assay Conditions 2.5.1 In Situ Incubation of Probe Substrates with Cultured Human Hepatocytes Incubations of hepatocytes with probe substrates were conducted in accordance with SOP L5041.02. Approximately 24 hours after the last treatment, spent media was aspirated from the wells, and each well was rinsed two times with pre-warmed (37±2° C.) fresh culture media. Media was aspirated from the wells and reactions were started by addition of 200 µL pre-warmed media containing the probe substrate to each well. The culture multi-well plates were placed in a humidified culture chamber (37±1° C. at 95% relative humidity, 95/5% air/$CO_2$), and incubations were carried out for 30 minutes (Table 1). At 30 minutes, an aliquot (150 µL) of the incubation mixture was removed and added to a well of a 96-well plate containing 300 µL of stop reagent (acetonitrile) and internal standard (Table 2). The mixtures were mixed thoroughly and allowed to sit for at least 15 minutes at 2-8° C. Samples were centrifuged at 2000×g for 10 minutes at 2-8° C., and supernatant fractions were analyzed by LC/MS/MS. For each assay, incubations were carried out under the conditions indicated in Table 1.

TABLE 1

Summary of assay conditions to measure microsomal CYP enzyme activity

| Enzyme | Substrate | Substrate concentration (µM) | Substrate solvent (v/v, final incubation concentration) | Incubation time (min) |
|---|---|---|---|---|
| CYP1A2 | Phenacetin | 100 | Methanol (0.4%) | 30 |
| CYP3A4B | Midazolam | 30 | Methanol (1%) | 30 |

Incubation volume = 200 µL

| Chemical | Catalog number | Lot number | Storage conditions [a] | Vehicle | Purity | Supplier |
|---|---|---|---|---|---|---|
| DMSO | D2650 | 079K2305 089K2310 | Room temperature | Not applicable | Not applicable | Sigma-Aldrich |
| Omeprazole | O104 | 079K1584 | 2 to 8° C. | DMSO | 99% | Sigma-Aldrich |
| Rifampin | R3501 | 115K1498 | −20 ± 5° C. | DMSO | 100% | Sigma-Aldrich |
| Mibefradil | M5441 | 026K47034 | Room temperature | High purity water | 99% | Sigma-Aldrich |

[a] Storage conditions of neat compound.

TABLE 2

Summary of metabolite analysis by liquid chromatography tandem mass spectrometry

| Enzyme | Metabolite monitored | Ionization mode [a] | Analytical SOP followed | Internal standard | Internal standard concentration (ng/mL) [b] |
|---|---|---|---|---|---|
| CYP1A2 | Acetaminophen | ESI– | L8120.06 | Acetaminophen-$d_4$ | 300 |
| CYP3A4/5 | 1'-Hydroxymidazolam | ESI+ | L8170.05 | 1'-Hydroxymidazolam-$d_4$ | 1000 |

[a] Indicates the type of ionization (i.e., electrospray ionization [ESI]) and the polarity (+ or –).
[b] Value indicates the stock concentration of the internal standard. This concentration is diluted 16-fold when added to the stopped incubation mixture.

Standards and quality control samples were similarly prepared with the addition of authentic metabolite standards.

2.6 Analytical Methods
2.6.1 LC/MS/MS Methods

All analyses were performed with validated LC/MS/MS methods. The procedures used for the analysis of each metabolite followed the applicable LC/MS/MS analytical method SOPs and are summarized in Table 2. The MS equipment was either an ABI Sciex (Applied Biosystems/MDS SCIEX) API 4000 or API 3000 instrument with Shimadzu HPLC pumps and autosampler systems.

| Enzyme | Metabolite monitored | API instrument [a] | HPLC column [b] |
|---|---|---|---|
| CYP1A2 | Acetaminophen | 3000 | Waters Atlantis dC18 (5-µm, 100 mm × 2.1 mm) |
| CYP3A4/5 | 1'-Hydroxymidazolam | 4000 | |

[a] Model of LC/MS/MS system from Applied Biosystems/MDS SCIEX.
[b] All HPLC columns were preceded by a Phenomenex Luna C-8 guard column (4.0 mm × 2.0 mm).

Authentic metabolite standards were used, and deuterated metabolites were used as internal standards in all assays. Zero-time incubations served as blanks. Sample analysis, integration and reporting were conducted according to SOP L8013.02, L8020.02 and L8011.02 (XenoTech, LLC), respectively.

Metabolites were quantified by reference to a standard calibration curve based on back calculation of a weighted (1/x), linear, least-squares regression. The regression fit was based on the peak ratio of the analyte to internal standard calculated from calibration standard samples, which were prepared from authentic metabolite standards. Peak areas were integrated with Applied Biosystems/MDS SCIEX Analyst data system, version 1.4.2.

2.6.2 mRNA Analysis

Quantitative RT-PCR was carried out according to SOP L6160.04 (XenoTech, LLC) and the Applied Biosystems protocol. Each PCR was performed in triplicate. A Primer Mix was prepared for each Gene Expression assay. A typical Primer Mix contained TaqMan Universal Master Mix (1×), Gene Expression Assay (1×, 900 nM forward and reverse primers) and RNase-free water. The Reaction Mix was prepared by adding the Primer Mix to cDNA. A percentage of samples (no less than 10%) included NACs. (NACs are RNA samples that are not reverse transcribed and are used to show that mRNA, not genomic DNA, is the source of PCR's fluorescent signal.) Reactions were analyzed on an Applied Biosystems Real Time PCR sequence detection system (AB 7300 or AB 7900HT). The relative quantity of the target cDNA compared with that of the control cDNA (GAPDH) was determined by the ΔΔt method (Applied Biosystems User Bulletin #2). Relative quantification measures the change in mRNA expression in a test sample relative to that in a control sample (e.g., DMSO). This method assumes that the efficiency of the target amplification and the efficiency of the endogenous control amplification are approximately equal.

2.7 Data Processing

Data were processed and graphed with the computer program Microsoft Excel 2003 (Microsoft Inc.). Individual rates of reaction from like treatment groups were averaged, and for those groups with n≥3, standard deviations were determined. Fold increases were determined by dividing the enzymatic rate for each treatment group by that of the vehicle control. Percent positive control was calculated with the following equation:

$$\text{Percent positive control} = \frac{(\text{activity of test article treated cells} - \text{activity of vehicle control})}{(\text{activity of positive control} - \text{activity of vehicle control})} \times 100$$

For qRT-PCR, data were processed using the Sequence Detection System (SDS) Software version 1.4, for Relative Quantification (Applied Biosystems). This software analyzes relative gene expression using the comparative Ct method (ΔΔCt), which relates the PCR signal of the target transcript to the PCR signal of the target in an untreated control. Both the treated sample and the untreated control signals are normalized to the endogenous control (GAPDH), for which expression is not affected by treatment and expression is constant throughout the tissue being tested. The results of this method are expressed as a fold change in expression with respect to the target transcript expression in the untreated control.

Calculations are as follows:

$$\Delta Ct = Ct(\text{target}) - Ct(\text{endogenous control}) \qquad 1.$$

$$\Delta\Delta Ct = \Delta Ct(\text{treated sample}) - \Delta Ct(\text{untreated control}) \qquad 2.$$

$$\text{Fold change in expression} = 2 - \Delta\Delta Ct \qquad 3.$$

An algorithm within the software automatically removed outliers from analysis. The criteria for acceptance of data are proprietary to Applied Biosystems. Outliers are considered to be wells with Ct values that differ significantly from associated replicate wells and typically are wells that did not amplify sufficiently if at all.

The level of mRNA expression relative to the positive control was calculated as follows:

$$\text{Percent positive control} = \frac{[(\text{fold change in treated sample}) - 1]}{[(\text{fold change in positive control}) - 1]} \times 100$$

3. Results And Discussion

The effects of treating human hepatocytes with laquinimod and Compound 2 on CYP enzyme activity and mRNA levels are shown in Tables 3-7. Unless otherwise noted, the data in the figures and tables are presented as the mean±standard deviation of data from triplicate incubations from one human preparation, rounded to three significant figures. The average fold-increases are summarized in Tables 4 and 6. Fold increase is presented either as fraction of control or as fold increase over control, where the control refers to the corresponding vehicle-treated samples. Fold increase was rounded to three significant figures. Comparison of the test article to the prototypical inducer (percent positive control) is shown in Tables 5 and 7, and was rounded to three significant figures.

TABLE 3

CYP activity: The effects of treating cultured human hepatocytes with laquinimod, Compound 2 or prototypical inducers on in situ cytochrome P450 (CYP) enzyme activity

| | | Enzyme activity (pmol/mg protain/min) [a] | |
|---|---|---|---|
| Treatment | Concentration | Phenacetin O-dealkylation (CYP1A2) | Midazolam 1'-hydroxylation (CYP3A4/5) |
| Dimethyl sulfoxide | 0.1% (v/v) | 2.99 ± 0.13 | 0.195 ± 0.011 |
| Laquinimod | 0.01 μM | 25.2 ± 0.8 | 0.180 ± 0.023 |
| Laquinimod | 0.05 μM | 54.0 ± 4.5 | 0.161 ± 0.013 |
| Laquinimod | 0.1 μM | 65.1 ± 1.9 | 0.151 ± 0.002 |
| Laquinimod | 1 μM | 131 ± 12 | 0.106 ± 0.004 |
| Laquinimod | 10 μM | 183 ± 7 | 0.0957 ± 0.0067 |
| Compound 2 | 0.01 μM | 22.1 ± 2.7 | 0.179 ± 0.006 |
| Compound 2 | 0.05 μM | 31.6 ± 2.6 | 0.151 ± 0.009 |
| Compound 2 | 0.1 μM | 48.2 ± 2.4 | 0.140 ± 0.010 |
| Compound 2 | 1 μM | 90.8 ± 11.5 | 0.109 ± 0.010 |
| Compound 2 | 10 μM | 180 ± 8 | 0.101 ± 0.003 |
| Omeprazole | 100 μM | 84.9 ± 5.4 | NA |
| Mibefradil | 10 μM | 11.3 ± 2.1 | NA |
| Rifampin | 10 μM | NA | 0.941 ± 0.019 |

[a] Values are the mean ± standard deviation of triplicate determinations of human hepatocyte preparation H971 rounded to three significant figures.

TABLE 4

CYP activity fold increase: The effects of treating cultured human hepatocytes with laquinimod, Compound 2 or prototypical inducers on in situ cytochrome P450 (CYP) enzyme activity

| | | Fold Increase [a] | |
|---|---|---|---|
| Treatment | Concentration | Phenacetin O-dealkylation (CYP1A2) | Midazolam 1'-hydroxylation (CYP3A4/5) |
| Dimethyl sulfoxide | 0.1% (v/v) | 1.00 | 1.00 |
| Laquinimod | 0.01 μM | 8.43 | 0.92 |
| Laquinimod | 0.05 μM | 18.06 | 0.82 |
| Laquinimod | 0.1 μM | 21.75 | 0.78 |
| Laquinimod | 1 μM | 43.79 | 0.54 |
| Laquinimod | 10 μM | 61.02 | 0.49 |
| Compound 2 | 0.01 μM | 7.39 | 0.91 |
| Compound 2 | 0.05 μM | 10.54 | 0.77 |
| Compound 2 | 0.1 μM | 16.12 | 0.72 |
| Compound 2 | 1 μM | 30.36 | 0.56 |
| Compound 2 | 10 μM | 60.21 | 0.51 |
| Omeprazole | 100 μM | 28.38 | NA |
| Mibefradil | 10 μM | 3.76 | NA |
| Rifampin | 10 μM | NA | 4.82 |

[a] Values are the results of human hepatocyte preparation H971 rounded to three significant figures.

TABLE 5

CYP activity percent positive control: The effects of treating cultured human hepatocytes with laquinimod, Compound 2 or prototypical inducers on in situ cytochrome P450 (CYP) enzyme activity

| | | Percent positive control [a] | |
|---|---|---|---|
| Treatment | Concentration | Phenacetin O-dealkylation (CYP1A2) | Midazolam 1'-hydroxylation (CYP3A4/5) |
| Dimethyl sulfoxide | 0.1% (v/v) | 0 | 0 |
| Laquinimod | 0.01 μM | 27.1 | −2.04 |
| Laquinimod | 0.05 μM | 62.3 | −4.63 |
| Laquinimod | 0.1 μM | 75.8 | −5.89 |
| Laquininiod | 1 μM | 156 | −12.0 |
| Laquinimod | 10 μM | 219 | −13.4 |
| Compound 2 | 0.01 μM | 23.3 | −2.24 |
| Compound 2 | 0.05 μM | 34.9 | −5.94 |
| Compound 2 | 0.1 μM | 55.2 | −7.46 |
| Compound 2 | 1 μM | 107 | −11.5 |
| Compound 2 | 10 μM | 216 | −12.7 |
| Omeprazole | 100 μM | 100 | ND |
| Mibefradil | 10 μM | 10.1 | ND |
| Rifampin | 10 μM | ND | 100 |

[a] Values are the results of human hepatocyte preparation H971 rounded to three significant figures.
ND Not determined.
For CYP1A2, the positive control is omeprazole and the vehicle control is DMSO.
For CYP3A4/5, the positive control is rifampin and the vehicle control is DMSO.

TABLE 6 mRNA fold increase: The effects of treating cultured human hepatocytes with laquinimod, Compound 2 or prototypical inducers on microsomal cytochrome P450 (CYP) mRNA levels as determined by qRT-PCR (post in situ incubations)

| | | Fold increase [a] | |
|---|---|---|---|
| Treatment | Concentration | CYP1A2 | CYP3A4 |
| Dimethyl sulfoxide | 0.1% (v/v) | 1.00 | 1.00 |
| Laquinimod | 0.01 μM | 4.22 | 0.621 |
| Laquinimod | 0.05 μM | 7.90 | 0.347 |
| Laquinimod | 0.1 μM | 9.50 | 0.427 |
| Laquinimod | 1 μM | 16.8 | 0.286 |
| Laquinimod | 10 μM | 20.5 | 0.636 |
| Compound 2 | 0.01 μM | 2.84 | 0.437 |
| Compound 2 | 0.05 μM | 4.98 | 0.428 |
| Compound 2 | 0.1 μM | 7.20 | 0.339 |
| Compound 2 | 1 μM | 13.1 | 0.252 |
| Compound 2 | 10 μM | 24.3 | 0.689 |
| Omeprazole | 100 μM | 8.58 | NT |
| Mibefradil | 10 μM | 0.423 | NT |
| Rifampin | 10 μM | NT | 4.63 |

[a] Values are the results of human hepatocyte preparation H971 rounded to three significant figures.
NT Not tested by study design.

TABLE 7 mRNA percent positive control: The effects of treating cultured human hepatocytes with laquinimod, Compound 2 or prototypical inducers on microsomal cytochrome P450 (CYP) mRNA levels as determined by qRT-PCR (post in situ incubations)

| | | Percent positive control [a] | |
|---|---|---|---|
| Treatment | Concentration | CYP1A2 | CYP3A4 |
| Dimethyl sulfoxide | 0.1% (v/v) | 0 | 0 |
| Laquinimod | 0.01 μM | 42.5 | −10.4 |
| Laquinimod | 0.05 μM | 91.1 | −18.0 |
| Laquinimod | 0.1 μM | 112 | −15.8 |
| Laquinimod | 1 μM | 209 | −19.7 |

TABLE 7-continued mRNA percent positive control: The effects of treating cultured
human hepatocytes with laquinimod, Compound 2 or prototypical
inducers on microsomal cytochrome P450 (CYP) mRNA levels as
determined by qRT-PCR (post in situ incubations)

| Treatment | Concentration | Percent positive control [a] | |
|---|---|---|---|
| | | CYP1A2 | CYP3A4 |
| Laquinimod | 10 µM | 257 | −10.0 |
| Compound 2 | 0.01 µM | 24.2 | −15.5 |
| Compound 2 | 0.05 µM | 52.5 | −15.8 |
| Compound 2 | 0.1 µM | 81.7 | −18.2 |
| Compound 2 | 1 µM | 159 | −20.6 |
| Compound 2 | 10 µM | 307 | −8.57 |
| Omeprazole | 100 µM | 100 | ND |
| Mibefradil | 10 µM | −7.61 | ND |
| Rifampin | 10 µM | ND | 100 |

[a] Values are the results of human hepatocyte preparation H971 rounded to three significant figures.
ND Not determined
For CYP1A2, the positive control is omeprazole and the vehicle control is DMSO.
For CYP3A4, the positive control is rifampin and the vehicle control is DMSO.

3.1 Viability and Morphology of Cultured Human Hepatocytes

At the time of isolation the viability of the human hepatocyte preparation was 70.9%. During and after the 72-hour adaptation period, the culture was observed daily by light microscopy and judged to be morphologically normal with confluency adequate for treatment with test and control articles. Within 24 hours after the final treatment, hepatocytes were photographed to document their morphological integrity and any overt signs of toxicity of the test articles. Representative photomicrographs are maintained at the Testing Facility. These photomicrographs show that, in general, human hepatocytes treated with vehicle (DMSO), laquinimod and Compound 2 or known CYP inducers exhibited normal hepatocyte morphology. Prior to and during treatment, human hepatocyte cultures formed confluent monolayers with few intercellular spaces; they were cuboidal contained intact cell membranes and granular cytoplasm with one or two centrally located nuclei. Treatment of human hepatocyte culture H971 with laquinimod, Compound 2 or laquinimod and mibefradil resulted in no changes in cell morphology.

3.2 The Effect of Laquinimod and Compound 2 on Human CYP1A2 Activity and mRNA Levels Determination of Phenacetin O-Dealkylase (CYP1A2) Activity In cultured human hepatocytes, phenacetin O-dealkylation is catalyzed by CYP1A2, which is the major omeprazole-inducible CYP enzyme. The effects of treating cultured human hepatocytes with laquinimod or Compound 2 on in situ phenacetin O-dealkylase (CYP1A2) activity are shown in Table 3 and summarized in Table 4. Treatment of cultured human hepatocytes once daily for three consecutive days with omeprazole caused, on average, a 28.4-fold increase in phenacetin O-dealkylase (CYP1A2) activity.

Treatment of hepatocyte culture H971 with laquinimod (up to 10 µM) caused a concentration-dependent increase, up to 61.0-fold in CYP1A2 activity compared to the vehicle control. At the concentrations tested (0.01 µM to 10 µM), laquinimod was 21.7% to 291% as effective as the positive control omeprazole, at inducing CYP1A2 activity. In addition, treatment, once daily for three consecutive days with mibefradil alone resulted in a 3.76-fold increase in CYP1A2 activity.

Furthermore, treatment of hepatocyte culture H971 with Compound 2 (up to 10 µM) caused a concentration-dependent increase up to 60.2-fold in CYP1A2 activity compared to the vehicle control. At the concentrations tested (0.01 µM to 10 µM), Compound 2 was 23.3% to 216% as effective as the positive control omeprazole, at inducing CYP1A2 activity.

Determination of CYP1A2 mRNA Levels

The effects of treating cultured human hepatocytes with laquinimod and Compound 2 on CYP1A2 mRNA expression are shown in Table 6. Treatment of cultured human hepatocytes once daily for three consecutive days with omeprazole caused, on average, an 8.58-fold increase in CYP1A2 mRNA levels.

Similar to CYP1A2 activity, treatment of hepatocyte culture H971 with laquinimod (up to 10 µM) caused a concentration-dependent increase up to 20.5-fold in CYP1A2 mRNA levels compared to the vehicle control. At the concentrations tested (0.01 µM to 10 µM), laquinimod was 42.5% to 257% as effective as the positive control omeprazole, at inducing CYP1A2 mRNA levels. Contrary to CYP1A2 activity, treatment, once daily for three consecutive days with mibefradil alone caused a 57.7% decrease in CYP1A2 mRNA levels, compared to vehicle control.

Furthermore, treatment of hepatocyte culture H971 with Compound 2 (up to 10 µM) caused a concentration-dependent increase, up to 24.3-fold in CYP1A2 mRNA levels compared to the vehicle control. At the concentrations tested (0.01 µM to 10 µM), Compound 2 was 24.2% to 307% as effective as the positive control omeprazole, at inducing CYP1A2 mRNA levels.

3.3 The Effect of Laquinimod and Compound 2 on Human CYP3A4/5 Activity and CYP3A4 mRNA Levels Determination of Midazolam 1'-Hydroxylase (CYP3A4/5) Activity In cultured human hepatocytes, midazolam 1'-hydroxylation is catalyzed by CYP3A4/5. CYP3A4 is the major rifampin-inducible CYP enzyme. The effects of treating cultured human hepatocytes with laquinimod and Compound 2 on in situ midazolam 1'-hydroxylase (CYP3A4/5) activity are shown in Table 3 and summarized in Table 4. Treatment of cultured human hepatocytes once daily for three consecutive days with rifampin caused an increase (4.92-fold) in midazolam 1'-hydroxylase activity.

Treatment of hepatocyte culture H971 with either laquinimod (up to 10 µM) or Compound 2 (up to 10 µM) caused a concentration-dependent decrease in CYP3A4/5 activity by 50.9% and 48.2%, respectively, compared to the vehicle control.

Determination of CYP3A4 mRNA Levels

The effects of treating cultured human hepatocytes with laquinimod and Compound 2 on CYP3A4 mRNA expression are shown in Table 6. Treatment of cultured human hepatocytes once daily for three consecutive days with rifampin caused a 4.63-fold increase in CYP3A4 mRNA levels.

Similar to CYP3A4/5 activity, treatment of hepatocyte culture H971 with either laquinimod (up to 10 µM) or Compound 2 (up to 10 µM) caused a concentration-dependent decrease by 36.4% and 31.1% compared to the vehicle control, respectively in CYP3A4 mRNA levels.

Determination of Compound 2 or Laquinimod to DELAQ Ratio

The concentrations of Compound 2, laquinimod and DELAQ were measured in spent media aliquots from media collected just prior to treatment, on each day of treatment, and just prior to incubation of the marker substrates. The concentration of formed DELAQ was approximately 2-fold higher in the laquinimod media compared to the Compound 2 media. At the 10 µM treatment concentrations of either Compound 2 or laquinimod, the ratio of Compound 2:DELAQ was on average, 40.9 while the ratio of laquinimod:DELAQ was on average, 15.7. This represents an approximately 3-fold increase in the formation of DELAQ from laquinimod compared to Compound 2 and is explained by the presence of deuterium on the ethyl moiety which results in slower N-deethylation.

4. Conclusions

In conclusion, under conditions where prototypical inducers caused anticipated and appropriate increases in CYP activity and mRNA levels, treatment with up to 10 μM laquinimod or Compound 2 (deuterated analog of laquinimod) caused similar concentration-dependent increases in CYP1A2 activity and mRNA levels and a concentration-dependent decrease in CYP3A4/5 activity and CYP3A4 mRNA levels, but an approximate 3-fold difference in the Compound 2:DELAQ to laquinimod:DELAQ ratio was observed.

What is claimed is:

1. A method of treating a human subject afflicted with an autoimmune disease comprising administering to the human subject 0.2 mg-2.0 mg per day of a deuterium-enriched compound having the structure:

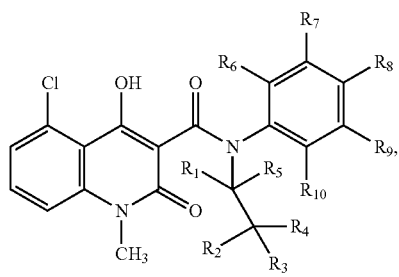

wherein each of R1-R10 is independently H or D, and at least one of R1-R10 is D, or a pharmaceutically acceptable salt thereof, effective to treat the subject.

2. The method of claim 1, wherein the deuterium-enriched compound is

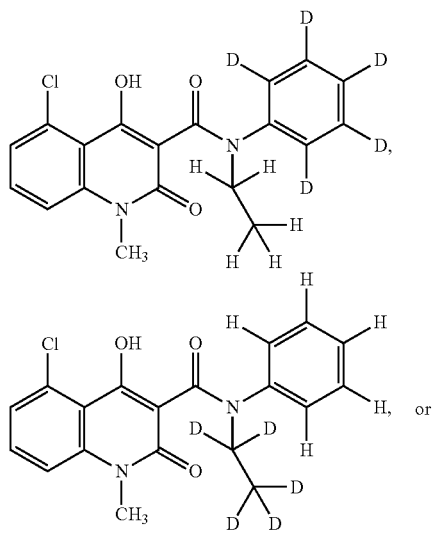

or a pharmaceutically acceptable salt thereof.

3. The method of claim 2, wherein the deuterium-enriched compound is

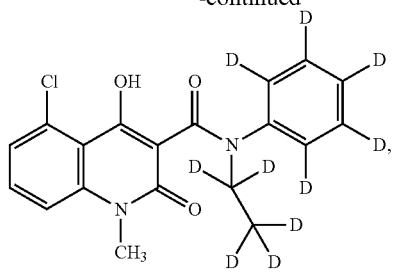

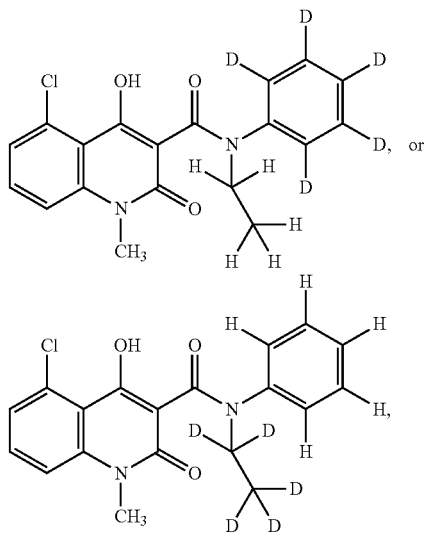

or a pharmaceutically acceptable salt thereof.

4. The method of claim 3, wherein the deuterium-enriched compound is

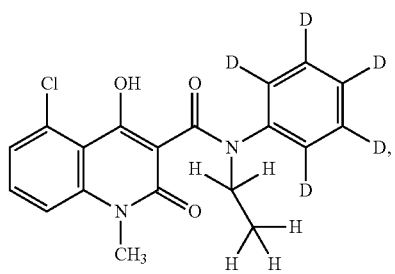

or a pharmaceutically acceptable salt thereof.

5. The method of claim 1, wherein the autoimmune disease is Multiple Sclerosis, systemic Lupus Erythematosus, lupus nephritis, lupus arthritis, Crohn's Disease or Rheumatoid arthritis.

6. The method of claim 5, wherein toe autoimmune disease is Multiple Sclerosis.

7. The method of claim 1, wherein administration of the deuterium-enriched compound is more effective in treating the autoimmune disease than administration of an equivalent molar amount of non-deuterium-enriched laquinimod.

8. The method of claim 1, wherein the level of optionally deuterated 5-chloro-4-hydroxy-1-methyl-2-oxo-N-phenyl-1,2-dihydroquinoline-3-carboxamide formed in the human subject upon administration of the deuterium-enriched compound is reduced, compared to the level of 5-chloro-4-hydroxy-1-methyl-2-oxo-N-phenyl-1,2-dihydroquinoline-3-carboxamide formed when an equivalent molar amount of non-deuterium-enriched laquinimod is administered to the human subject.

9. The method of claim 8, wherein the level of optionally deuterated 5-chloro-4-hydroxy-1-methyl-2-oxo-N-phenyl-1,2-dihydroquinoline-3-carboxamide is reduced by at least 50%.

10. The method of claim 9, wherein the level of optionally deuterated 5-chloro-4-hydroxy-1-methyl-2-oxo-N-phenyl-1,2-dihydroquinoline-3-carboxamide is reduced by at least 90%.

11. A method of inducing reduced formation of optionally deuterated 5-chloro-4-hydroxy-1-methyl-2-oxo-N-phenyl-1,2-dihydroquinoline-3-carboxamide in a human subject comprising administering to the human subject a therapeutically effective amount of a deuterium-enriched compound having the structure:

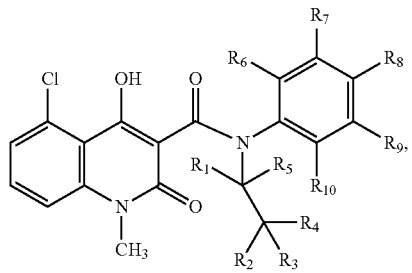

wherein each of R1-R10 is independently H or D, and at least one of R1-R10 is D, or a pharmaceutically acceptable salt thereof, wherein the reduced formation is relative to formation of 5-chloro-4-hydroxy-1-methyl-2-oxo-N-phenyl-1,2-dihydroquinoline-3-carboxamide upon administration of an equivalent molar amount of non-deuterium-enriched laquinimod.

12. The method of claim 11, wherein the level of optionally deuterated 5-chloro-4-hydroxy-1-methyl-2-oxo-N-phenyl-1,2-dihydroquinoline-3-carboxamide is reduced by at least 50%, compared to the level of 5-chloro-4-hydroxy-1-methyl-2-oxo-N-phenyl -1,2-dihydroquinoline-3-carboxamide formed when an equivalent molar amount of non-deuterium-enriched laquinimod is administered to the human subject.

13. The method of claim 12, in the level of optionally deuterated 5-chloro-4-hydroxy-1-methyl-2-oxo-N-phenyl-1,2-dihydroquinoline-3-carboxamide is reduced by at least 90%.

14. A mixture of at least two different deuterium-enriched compounds, each compound having the structure:

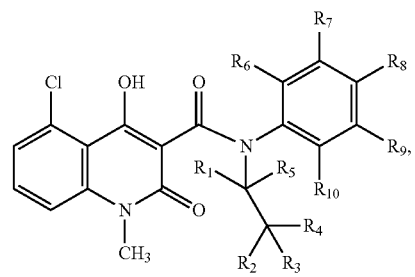

wherein each of R1-R10 is independently H or D, and each of the at least two deuterium-enriched compounds contains D at a different R1-R10, or pharmaceutically acceptable salts thereof.

15. The mixture of claim 14, wherein one of the at least two deuterium-enriched compounds has the structure:

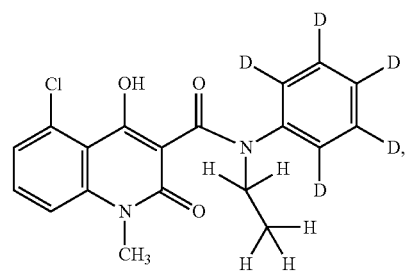

or pharmaceutically acceptable salts thereof.

16. The mixture of 14, wherein one of the at least enriched compounds has the structure:

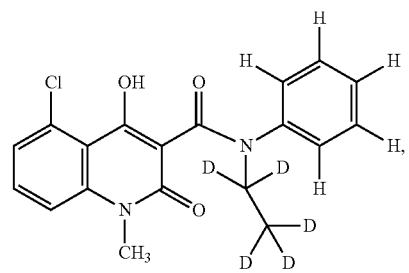

pharmaceutically acceptable salts thereof.

17. The mixture of claim 14, wherein one of the at least two deuterium-enriched compounds has the structure:

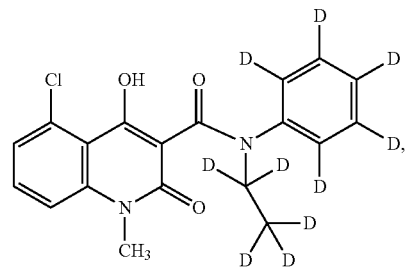

or pharmaceutically acceptable salts thereof.

18. A pharmaceutical composition comprising the mixture of claim 14, or a pharmaceutically acceptable salt thereof, and a pharmaceutically acceptable carrier.

19. A pharmaceutical composition comprising a mixture of:
a) deuterium-enriched laquinimod or a pharmaceutically acceptable salt thereof;
b) at least one pharmaceutically acceptable carrier; and
c) a compound having the structure:

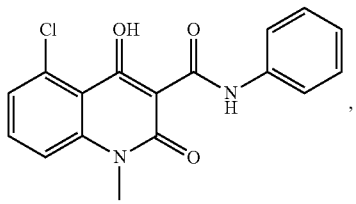

present in an amount w is less than 0.1% based on the combined weight of the compound and deuterium-enriched laquinimod.

20. The pharmaceutical composition of claim 19, wherein the compound is present in an amount less than 3 ppm based on the combined weight of the compound and deuterium-enriched laquinimod.

21. The pharmaceutical composition of claim 20, wherein the compound is present in an amount less than 2 ppm based on the combined weight of the compound and deuterium-enriched laquinimod.

22. The pharmaceutical composition of claim 19, wherein the deuterium-enriched laquinimod has the structure:

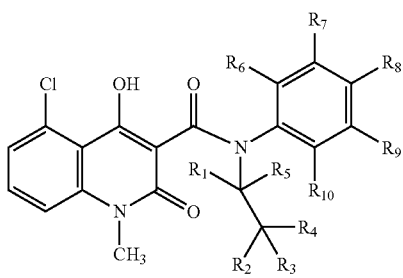

wherein each of R1-R10 is independently H or D, and at least one of R1-R10 is D, or a pharmaceutically acceptable salt thereof.

23. The pharmaceutical. composition of claim 22, wherein in the deuterium-enriched laquinimod, each of R1-R5 is D and each of R6-R10 is H, or a pharmaceutically acceptable salt thereof.

24. The pharmaceutical composition of claim 22, wherein the deuterium-enriched laquinimod, each of R1-R5 is H and each of R6-R10 is D, or a pharmaceutically acceptable salt thereof.

25. The pharmaceutical composition of claim 22, wherein in the deuterium-enriched laquinimod, each of R1-R10 is D, or a pharmaceutically acceptable salt thereof.

26. The pharmaceutical composition of claim 18 in the form of a tablet.

27. The pharmaceutical composition of claim 18, which when ingested by a human subject, provides a reduced level of optionally deuterated 5-chloro-4-hydroxy-1-methyl-2-oxo-N-phenyl-1,2-dihydroquinoline-3-carboxamide formed in the human subject, relative to the level of 5-chloro-4-hydroxy-1-methyl-2-oxo-N-phenyl-1,2-dihydroquinoline-3-carboxamide formed when an equivalent molar amount of non-deuterium-enriched laquinimod is ingested by the human subject.

28. A process for preparing the pharmaceutical composition of claim 18, comprising:
a) obtaining a batch of deuterium-enriched laquinimod or a pharmaceutically acceptable salt thereof;
b) determining by apparatus the total amount of optionally deuterated 5-chloro-4-hydroxy-1-methyl-2-oxo-N-phenyl-1,2-dihydroquinoline-3-carboxamide present in the batch of deuterium-enriched laquinimod or a pharmaceutically acceptable salt thereof; and
c) preparing the pharmaceutical composition using the batch only if the batch is determined to have less than 0.1% by weight of optionally deuterated 5-chloro-4-hydroxy-1-methyl-2-oxo-N-phenyl-1,2-dihydroquinoline-3-carboxamide.

29. A process for producing a validated batch of the pharmaceutical composition of claim 18 for distribution comprising:
a) obtaining a batch of the pharmaceutical composition;
b) determining by apparatus the total amount of optionally deuterated 5-chloro-4-hydroxy-1-methyl-2-oxo-N-phenyl-1,2-dihydroquinoline-3-carboxamide in a sample of the batch; and
c) validating the batch for distribution only if the sample of the batch is determined to contain less than 0.1% by weight of optionally deuterated 5-chloro-4-hydroxy-1-methyl-2-oxo-N-phenyl-1,2-dihydroquinoline-3-carboxamide relative to the combined weight of laquinimod and optionally deuterated 5-chloro-4-hydroxy-1-methyl-2-oxo-N-phenyl-1,2-dihydroquinoline-3-carboxamide.

* * * * *